(12) United States Patent
Kume et al.

(10) Patent No.: US 10,000,739 B2
(45) Date of Patent: Jun. 19, 2018

(54) METHOD AND CULTURE MEDIUM FOR IMPROVING PLURIPOTENT STEM CELL DIFFERENTIATION INDUCING EFFICIENCY

(75) Inventors: Shoen Kume, Kumamoto (JP); Fumio Endo, Kumamoto (JP); Nobuaki Shiraki, Kumamoto (JP); Yasuko Shiraki, Kumamoto (JP); Kazuhiko Kume, Kumamoto (JP)

(73) Assignee: NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 589 days.

(21) Appl. No.: 13/881,678

(22) PCT Filed: Oct. 20, 2011

(86) PCT No.: PCT/JP2011/074206
§ 371 (c)(1),
(2), (4) Date: May 15, 2013

(87) PCT Pub. No.: WO2012/056997
PCT Pub. Date: May 3, 2012

(65) Prior Publication Data
US 2013/0252335 A1   Sep. 26, 2013

(30) Foreign Application Priority Data
Oct. 28, 2010   (JP) ................................. 2010-242774

(51) Int. Cl.
C12N 5/071   (2010.01)
(52) U.S. Cl.
CPC ........... *C12N 5/067* (2013.01); *C12N 5/0602* (2013.01); *C12N 2500/32* (2013.01); *C12N 2506/02* (2013.01); *C12N 2506/45* (2013.01); *C12N 2533/52* (2013.01)
(58) Field of Classification Search
CPC ... C12N 5/067; C12N 2500/32; C12N 5/0602
See application file for complete search history.

(56) References Cited

U.S. PATENT DOCUMENTS

2012/0058491 A1   3/2012   Kume et al.

FOREIGN PATENT DOCUMENTS

| JP | 2005-095027 | 4/2005 |
|---|---|---|
| JP | 2009-100702 | 5/2009 |
| WO | WO 2006/126574 | 11/2006 |
| WO | WO 2007/102787 | 9/2007 |
| WO | WO 2007/130474 | 11/2007 |
| WO | WO 2008/149807 | 11/2008 |
| WO | 2009/018453 | 2/2009 |
| WO | 2010/059775 | 5/2010 |

OTHER PUBLICATIONS

Dhara et al (Differentiation (2008) 76:454-464).*
Stachelscheid (Thesis: 1-116, 2009).*
D'Amour et al (Nat Biotechnol, 23 (12): 1534-1541, 2005.*
Brevini et al., 2010, Theriogenology, vol. 74, pp. 544-550.*
Paris et al, (Theriogenology, 74: 516-524, 2010).*
Munoz et al, (Theriogenology, 69: 1159-1164, 2008).*
Block (Life enhancement, p. 1-11, 2012).*
Patel et al, Stem Cell Rev, 6(3): 367-380, 2010).*
Djuric et al (Stem Cell Research & Therapy, 1:3-6, 2010).*
Yu et al. (Science, 318: 1917-1920, 2007).*
Kajiwara et al (PNAS, 109: 12538-12543, 2012).*
Osafune et al (Nat Biotechnol, 26: 313-315, 2008).*
Smith et al., "Inhibition of pluripotential embryonic stem cell differentiation by purified polypeptides," Nature, 336: 688-90, 1988.
Takahashi K.,et al., "Induction of pluripotent stem cells from adult human fibroblasts by defined factors," Cell, 131: 861-872, 2007.
Wang et al., "Dependence of mouse embryonic stem cells on threonine catabolism," Science, 325: 435-439, 2009.
Kubo A, et al. "Development of definitive endoderm from embryonic stem cells in culture," Development, 131: 1651-1662,2004.
D'Amour Ka, et al. "Production of pancreatic hormone-expressing endocrine cells from human embryonic stem cells," Nat Biotechnol 24: 1392-1401, 2006.
Shiraki, N., et al. "Guided differentiation of Embryonic Stem cells into Pdx1-expressing regional specific definitive endoderm," Stem Cells, 26: 874-885, 2008.
Yoshida T., et al. "Expression patterns of Epiplakin1 in pancreas, pancreatic cancer and regenerating pancreas," Genes Cells, 13: 667-678, 2008.
Osafune K., et al. "Marked differences in differentiation propensity among human embryonic stem cell lines," Nat Biotechnol., 26: 313-315, 2008.
Wataya, T et al., Minimization of exogenous signals in ES cell culture induces rostral hypothalamic differentiation. Proc Natl Acad Sci, vol. 05(33), pp. 11796-11801 (2008).
Shiraki, N et al., "Guiding ES cell differentiation into the definitive endoderm lineages," Inflammation and Regeneration, vol. 30(2), pp. 109-114 (2010).
Higuchi et al., "Synthesized basement membranes direct the differentiation of mouse embryonic stem cells into pancreatic lineages," J Cell Sci vol. 123(Pt 16), pp. 2733-2742 2010.

(Continued)

*Primary Examiner* — Anoop K Singh
(74) *Attorney, Agent, or Firm* — Hunton Andrews Kurth LLP

(57) ABSTRACT

The purpose of the present invention is to provide a method and a culture medium which are capable of efficiently inducing the differentiation of pluripotent stem cells such as ES cells and iPS cells into desired cells by a simple means. The differentiation of pluripotent stem cells can be induced by culturing mammal-derived pluripotent stem cells in a differentiation culture medium that does not contain at least one amino acid selected from the group consisting of methionine, leucine, cysteine, tyrosine and arginine. Also provided is a differentiation-inducing culture medium which does not contain at least one amino acid selected from the group consisting of methionine, leucine, cysteine, tyrosine and arginine.

6 Claims, 18 Drawing Sheets

(56) References Cited

OTHER PUBLICATIONS

Shiraki, N et al., "Differentiation and characterization of embryonic stem cells into three germ layers," Biochem Biophys Res Commun vol. 381(4), pp. 694-699 (2009).

Translation of International Preliminary Report on Patentability for Internation Application No. PCT/JP2011/074206 dated May 14, 2013.

Deval C., et at., "Amino-acid limitation induces the GCN2 signaling pathway in myoblasts but not in myotubes", Biochimie, Masson, Paris, Fr., 90(11-12), Nov. 1, 2008, pp. 1716-1721.

Pohjanpelto P., et al., "Deprivation of a single amino acid induces protein synthesis-dependent increases in c-jun, c-myc, and ornithine decarboxylase mRNAs in Chinese hamster ovary cells." Mol. Cell. Biol., vol. 10(11), Nov. 1, 1990, pp. 5814-5821.

Bruhat A., et al., "Amino acid limitation regulates gene expression", Proceedings of the Nutrition Society, 58(3), Aug. 1, 1999, pp. 625-632.

Jousse C., et al., "Amino acid limitation regulates CHOP expression through a specific pathway independent of the unfolded protein response", Febs Letters, Elsevier, Amsterdam, NL, 448(2-3), Apr. 9, 1999, pp. 211-216.

Jones H.N., et al. "Expression and adaptive regulation of amino acid transport system A in a placental cell line under amino acid restriction" Reproduction, 131(5), May 1, 2006, pp. 951-960.

Wang J., et al., "Metabolic specialization of mouse embryonic stem cells", Cold Spring Harbor Symposia on Quantitative Biology, 76(1), Jan. 1, 2011, pp. 183-193.

Fontanier-Razzaq N., et al., "Nutrient-gene interactions amino acid deficiency up-regulates specific mRNAs in murine embryonic cells 1", J. Nutr. Jan. 1, 2002, pp. 2137-2142.

Wang Z., et al., "Amino acid limitation induces down-regulation of WNT5a at transcriptional level" Biochemical and Biophysical Research Communications, Academic Press Inc., Orlando, FL US, 378(4), Jan. 23, 2009, pp. 789-794.

Ryu J.M., et al., "L-Threonine regulate G1/S phase transition of mouse embryonic stem cells via PI3K/Akt, MAPks, and mTORc pathways", Journal of Biological Chemistry, 286(27) May 6, 2011, pp. 23667-23678.

Shiraki N., et al. "Guiding ES cell differentiation into the definitive endoderm lineages" Inflammation and Regeneration, 30(2), Mar. 1, 2010. pp. 109-114.

Wang J., et al., "Dependence of mouse embryonic stem cells on threonine catabolism" Science, 325(5939), Jul. 9, 2009, pp. 435-439.

Shan, J., et al., "Activation of the amino acid response modulates lineage specification during differentiation of murine embryonic stem cells", American Journal of Physiology: Endocrinology and Metabolism, American Physiological Society, Bethesda, MD US, 305(3), Aug. 1, 2013, pp. E325-E335.

Supplemental European Search Report issued in EP Application No. 11836133.6 dated May 8, 2014.

\* cited by examiner

METHOD AND CULTURE MEDIUM FOR IMPROVING PLURIPOTENT STEM CELL DIFFERENTIATION INDUCING EFFICIENCY

CROSS-REFERENCE TO RELATED APPLICATION(S)

The present application is based on and claims priority to PCT application No. PCT/JP2011/074206, filed on Oct. 20, 2011, which is based on and claims priority to Japanese Patent Application No. JP 2010-242774, filed on Oct. 28, 2010, and the entire disclosures of which are incorporated herein by reference in their entirety.

TECHNICAL FIELD

The present invention relates to a technology of inducing differentiation of pluripotent stem cells. More particularly, the present invention relates to a method and a culture medium for improving efficiency of inducing differentiation of pluripotent stem cells such as ES cells and iPS cells.

BACKGROUND ART

Since establishment in human of embryonic stem cells (ES cells) retaining pluripotency of being capable of differentiating into all cells in an individual and simultaneously having self-replication potential of being capable of infinitely proliferating, studies to induce in vitro differentiation of ES cells into principal body part cells are actively carried out.

Since production of human induced pluripotent stem cells (iPS cells) having pluripotency and self-replication potential together such as ES cells by introducing a specific gene into a somatic cell, studies to induce in vitro differentiation into principal body part cells using iPS cells in addition to ES cells are actively carried out.

For example, it is known that mouse ES cells can maintain an undifferentiating property by co-culturing on feeder cells such as mouse embryonic fibroblasts (MEF) and the like in the presence of a leukemia inhibitory factor (LIF) and if LIF is removed from a maintenance culture medium, differentiation of ES cells is induced (non-patent document 1).

On the other hand, it is reported that also human ES cells and human iPS cells can maintain undifferentiation by co-culturing on feeder cells such MEF and the like, and differentiation thereof is induced by transferring to a differentiation culture medium (non-patent document 2).

Further, it is reported that since a threonine dehydrogenase gene is expressed remarkably in mouse ES cells, proliferation of the cells depends on the metabolism of threonine as one of amino acids (non-patent document 3).

ES cells and iPS cells are useful models for study of gene functions in the development stage and possibly become medical transplantable cell sources because of pluripotency thereof, therefore, application of ES cells and iPS cells to regenerative medicine is expected. However, control of differentiation is necessary for use of ES cells and iPS cells in cell replacement therapies and tissue transplantation in diseases such as, for example, diabetes mellitus and the like.

Then, studies to control differentiation from undifferentiated cells into tissue cells are actively conducted recently. For example, there is a report on in vitro production of endoderm cells and insulin-producing cells from mouse and human ES cells (non-patent document 4, non-patent document 5).

Further, there are reports on a method of efficiently inducing differentiation of ES cells into pancreatic precursor cells by using mouse mesonephric cell line M15 cells as a supporting cell and adding activin•FGF (fibroblast growth factor)•retinoic acid to the culture medium (patent document 1, non-patent document 6) and on a method of efficiently inducing differentiation of mouse and human ES cells into hepatocytes, byway of culture conditions in which mmcM15 cells are used as a supporting cell and specific secreted growth factors (FGF and BMP (Bone Morphogenetic Proteins)) are added or eliminated (patent document 2, non-patent document 7).

When differentiation of ES cells and iPS cells into various cells is induced, however, undifferentiated stem cells partially remain and mix. In regenerative medicine, there is fear regarding safeness such as a possibility of canceration of such cells. For this reason, there is a need for a technology of eliminating undifferentiated cells in differentiated cells or of preventing mixing of undifferentiated cells by increasing differentiation induction efficiency.

There are various methods suggested for confirming mixing of undifferentiated cells or for selection thereof.

For example, there is a method of eliminating undifferentiated ES cells remaining after induction of differentiation, by utilizing a promoter of Stmt as an undifferentiation specific marker, thereby facilitating selection of undifferentiated ES cells remaining after induction of differentiation, and by removing the undifferentiated ES cells (patent document 3).

Further, there is a method of eliminating undifferentiated human embryonic stem cells in which undifferentiated human embryonic stem cells are identified by identifying cells expressing on its surface a podocalyxin like protein, and these cells are isolated (patent document 4).

It has recently reported that human ES cells and human iPS cells show a remarkable difference in differentiation potential between cell lines and, a tendency of differentiating into a specific family, that is, differentiation directionality varies for every cell line (non-patent document 8).

It is believed that banking of patient-derived iPS cell lines progresses in the field of regenerative medicine and it is expected that differentiation of many kinds of iPS cell lines into desired cells is induced, in the days ahead. It is supposed that if differentiation resistance is present between lines due to differentiation directionality for every line, when differentiation is induced under the same condition, differentiation induction efficiency lowers and undifferentiated cells mix in large amount and the like, affecting the nature of the final product. Accordingly, a method capable of efficiently inducing differentiation into intended tissue while avoiding differentiation resistance between lines is desired.

PRIOR ART DOCUMENT

Patent Document

Patent document 1: International Publication WO 2006/126574
Patent document 2: International Publication WO 2008/149807
Patent document 3: Japanese Unexamined Patent Application Publication No. 2005-095027
Patent document 4: Japanese Unexamined Patent Application Publication No. 2009-528838
Non-patent document 1: Smith et al., Inhibition of pluripotential embryonic stem cell differentiation by purified polypeptides. Nature, 336: 688-90, 1988.

Non-patent document 2: Takahashi K., Tanabe K., Ohnuki M., Narita M., Ichisaka T., Tomoda K. and Yamanaka S., Induction of pluripotent stem cells from adult human fibroblasts by defined factors. Cell, 131: 861-872, 2007.

Non-patent document 3: Wang et al., Dependence of mouse embryonic stem cells on threonine catabolism. Science, 325: 435-439, 2009.

Non-patent document 4: Kubo A, Shinozaki K, Shannon J M et al. Development of definitive endoderm from embryonic stem cells in culture. Development, 131: 1651-1662, 2004.

Non-patent document 5: D'Amour K A, Bang A G, Eliazer S et al. Production of pancreatic hormone expressing endocrine cells from human embryonic stem cells. Nat Biotechnol 24: 1392-1401, 2006.

Non-patent document 6: Shiraki, N., Yoshida, T., Araki, K., Umezawa A., Higuchi, Y., Goto H., Kume, K., and Kume, S. Guided differentiation of ES cells into Pdx1-expressing regional specific definitive endoderm. Stem Cells, 26: 874-885, 2008.

Non-patent document 7: Yoshida T., Shiraki N., Baba, H., Goto, M., Fujiwara, S., Kume K. and Kume S. The expression patterns of Epiplakin1 in pancreas, pancreatic cancer and regenerating pancreas. Genes Cells, 13: 667-678, 2008.

Non-patent document 8: Osafune K., Caron L., Borowiak M., Martinez R J., Fitz-Gerald C S., Sato Y., Cowan C A., Chien K R. and Melton D A. Marked differences in differentiation propensity among human embryonic stem cell lines. Nat. Biotechnol., 26: 313-315, 2008.

SUMMARY OF THE INVENTION

Problem to be Solved by the Invention

In the case of in vitro induction of differentiation of undifferentiated pluripotent stem cells such as ES cells and iPS cells into specific tissue cells, there is a problem of stay of undifferentiated cells which are indicted to cancerate easily. Further, human ES cells and human iPS cells have a problem that undifferentiated cells tend to remain, since differentiation directionality varies for every cell line.

The present invention has an object of providing a method and a culture medium which are capable of efficiently inducing the differentiation of pluripotent stem cells such as ES cells and iPS cells into desired cells by a simple means.

The present invention has another object of providing a method and a culture medium which are capable of preventing mixing of undifferentiated cells, by eliminating undifferentiated cells or increasing differentiation induction efficiency in inducing differentiation of pluripotent stem cells such as ES cells and iPS cells by a simple means.

Means for Solving the Problem

The present inventors have intensively studied to solve the above-described problem and resultantly found that differentiation can be efficiently induced by depriving a differentiation culture medium of a specific amino acid in inducing differentiation of pluripotent stem cells, leading to completion of the present invention.

That is, the present invention provides (1) A method of inducing differentiation of pluripotent stem cells, comprising culturing mammal-derived pluripotent stem cells in a differentiation culture medium which does not contain at least one amino acid selected from the group consisting of methionine and leucine as an essential amino acid and cysteine, tyrosine and arginine as a semi-essential amino acid in the culture medium, (2) The method of inducing differentiation of pluripotent stem cells according to (1), comprising culturing mammal-derived pluripotent stem cells in a differentiation culture medium which does not contain methionine or leucine as an essential amino acid or both the amino acids, (3) The method of inducing differentiation of pluripotent stem cells according to (2), comprising culturing mammal-derived pluripotent stem cells in a differentiation culture medium which does not contain methionine, (4) The method of inducing differentiation of pluripotent stem cells according to (1), comprising culturing mammal-derived pluripotent stem cells in a differentiation culture medium which does not contain at least one amino acid selected from the group consisting of cysteine, tyrosine and arginine as a semi-essential amino acid, (5) The method of inducing differentiation of pluripotent stem cells according to any one of (1) to (4), wherein the mammal-derived pluripotent stem cells are ES cells or iPS cells, (6) The method of inducing differentiation of pluripotent stem cells according to (5), wherein the mammal is human or mouse, (7) The method of inducing differentiation of pluripotent stem cells according to (6), wherein the mammal-derived pluripotent stem cells are human ES cells or human iPS cells, (8) The method of inducing differentiation of pluripotent stem cells according to any one of (1) to (4), comprising culturing ES cells or iPS cells in the above-described differentiation culture medium for at least 5 hours, preferably 1 day, further preferably 2 days, (9) The method of inducing differentiation of pluripotent stem cells according to any one of (1) to (4), wherein the above-described differentiation culture medium is an endoderm differentiation culture medium,

(10) The method of inducing differentiation of pluripotent stem cells according to any one of (1) to (4), comprising culturing the above-described pluripotent stem cells previously in a differentiation inducing culture medium containing essential amino acids (threonine, methionine, valine, leucine, isoleucine, phenylalanine, tryptophan, lysine and histidine) and semi-essential amino acids (cysteine, tyrosine and arginine),

(11) The method according to (10), comprising inducing differentiation of mammal-derived pluripotent stem cells into endoderm cells,

(12) The method according to (11), wherein the differentiated endoderm cells are further cultured in a liver differentiation culture medium, thereby differentiating the pluripotent stem cells into hepatocytes,

(13) The method according to (11), wherein the differentiated endoderm cells are further cultured in a pancreas differentiation culture medium, thereby differentiating the pluripotent stem cells into pancreatic cells,

(14) The method according to (12) or (13), wherein the above-described liver differentiation culture medium or pancreas differentiation culture medium is a differentiation culture medium containing proline added in an amount of 1 mM or more and 10 mM or less,

(15) The method according to any one of (10) to (14), wherein the pluripotent stem cells are human ES cells or human iPS cells,

(16) A culture medium for inducing differentiation of pluripotent stem cells, which does not contain at least one amino acid selected from the group consisting of methionine and leucine as an essential amino acid and cysteine, tyrosine and arginine as a semi-essential amino acid in the culture medium,

(17) The culture medium according to (16), wherein the pluripotent stem cells are human or mouse-derived ES cells or iPS cells,

(18) The culture medium according to (16), wherein the above-described culture medium for inducing differentiation is an endoderm differentiation culture medium for inducing differentiation of mouse or human-derived ES cells or iPS cells into endoderm cells,

(19) A method of inducing differentiation of pluripotent stem cells, comprising culturing mammal-derived pluripotent stem cells in a differentiation culture medium containing as an amino acid threonine, valine, isoleucine, phenylalanine, tryptophan, lysine and histidine as an essential amino acid and which does not contain at least one amino acid selected from the group consisting of methionine, leucine, cysteine, tyrosine and arginine in the culture medium,

(20) The method of inducing differentiation of pluripotent stem cells according to (8), wherein the culturing of ES cells or iPS cells in the above-described differentiation culture medium for at least 5 hours, preferably 1 day, further preferably 2 days is carried out directly before formation of endoderm cells obtained by induction of differentiation of the above-described pluripotent stem cells or in a period in which the formation can be confirmed,

(21) The differentiation inducing culture medium for inducing differentiation of pluripotent stem cells according to (16), containing as an amino acid threonine, valine, isoleucine, phenylalanine, tryptophan, lysine and histidine as an essential amino acid and which does not contain at least one amino acid selected from the group consisting of methionine, leucine, cysteine, tyrosine and arginine in the culture medium, and

(22) Use of a culture medium which does not contain at least one amino acid selected from the group consisting of methionine, leucine, cysteine, tyrosine and arginine in the culture medium, for inducing differentiation of pluripotent stem cells.

Effect of the Invention

By use of the method or culture medium of the present invention, differentiation of pluripotent stem cells such as ES cells and iPS cells can be efficiently induced, and mixing of undifferentiated cells can be reduced or eliminated. Further, by use of the method or culture medium of the present invention, an improvement in differentiation induction efficiency can be attained.

BRIEF EXPLANATION OF DRAWINGS

FIG. 3A is a view showing the culture schedule. FIG. 3B shows the results in a control culture medium (expression of Sox17 (red) and Oct3/4 (green) on Day 4, Day 6, Day 8 and Day 10 of culturing).

FIG. 7A is a view showing the culture schedule. FIG. 7B is a view showing the proportions of Oct3/4 positive cells and AFP positive cells in human iPS cells cultured using a liver differentiation culture medium after culturing using a methionine-deprived culture medium and culture media added with various concentrations of methionine. X axis represents the methionine addition concentration and Y axis represents the proportion of Oct3/4 or AFP positive cells (the proportion of the positive cells based on those stained with DAPI was calculated). The black bar represents the proportion of Oct3/4 positive cells and the white bar represents the proportion of AFP positive cells. FIG. 7C is an immunofluorescent stained image of human iPS cells on Day 20 cultured using a liver differentiation culture medium after culturing using a methionine-deprived culture medium and culture media added with various concentrations of methionine. The upper stage represents the results of staining with an anti-AFP antibody, showing AFP positive cells (green) and the lower stage represents the results of staining with an anti-Oct3/4 antibody, showing Oct3/4 positive cells (red).

FIG. 8A represents the results of immunofluorescent staining with an anti-AFP antibody and an anti-Oct3/4 antibody, of human iPS cells cultured for 20 days. Green represents AFP positive cells and red represents Oct3/4 positive cells. FIG. 8B represents the results of immunofluorescent staining with an anti-AFP antibody and an anti-albumin antibody, of human iPS cells cultured for 30 days. Green represents AFP positive cells and red represents secreted albumin. FIG. 8C represents the results of an indocyanine green (ICG) uptake-excretion test on Day 30. FIG. 8D represents the results of measurement of the albumin secretion volume on Day 20 and Day 30. FIG. 8E represents the results of examination of CYP3A4 activity on Day 30. FIG. 8F represents the results of PAS staining for human iPS cells cultured for 30 days.

In FIG. 9A, the upper stage represents the results of immunofluorescent staining with an anti-Oct3/4 antibody and an anti-Sox17 antibody of human iPS cells on Day 10 (red represents Sox17 positive cells and green represents Oct3/4 positive cells), and the lower stage represents the results of immunofluorescent staining with an anti-Oct3/4 antibody and an anti-Pdx1 antibody of human iPS cells on Day 13 (red represents Pdx1 positive cells and green represents Oct3/4 positive cells). FIG. 9B represents the results of RT-PCR for expression of Sox17, Oct3/4 and Pdx1 (expression of GAPDH was confirmed as control).

FIG. 10A represents the culture schedule. FIG. 10B represents the results of immunofluorescent staining with an anti-Sox17 antibody and an anti-Oct3/4 antibody, of cells on Day 10 of culturing. Red represents Sox17 positive cells and green represents Oct3/4 positive cells. FIG. 10C represents the results of RT-PCR for expression of Oct3/4, albumin and AFP, of cells on Day 18 of culturing (expression of GAPDH was confirmed as control). FIG. 10D represents the results of measurement of the albumin secretion volume on Day 17, Day 25 and Day 27.

FIG. 13A is a view showing the culture schedule. FIG. 13B represents the results of immunofluorescent staining with an anti-Sox17 antibody (red) and an anti-Oct3/4 antibody (green), of human iPS cells (Toe cell line) cultured in a methionine-deprived culture medium on Days 4 to 6, and FIG. 13C represents the results thereof, of human iPS cells (Toe cell line) cultured in a methionine-deprived culture medium on Days 8 to 10.

FIG. 14A represents the bright-field image of a cell colony and FIG. 14B represents the quantified number of cells.

FIG. 15A represents the results of evaluation of cell proliferation using a Click-iT EdU cell proliferation assay kit (Invitrogen), and FIG. 15B represents the results of evaluation of apoptosis using an In Situ Cell Death Detection Kit (Roche).

FIG. 18A represents the results of immunofluorescent staining with an anti-Sox17 antibody (red) and an anti-Oct3/4 antibody (green). FIG. 18B is a graph showing the quantitative results thereof.

DESCRIPTION OF EMBODIMENTS

Figure 1:
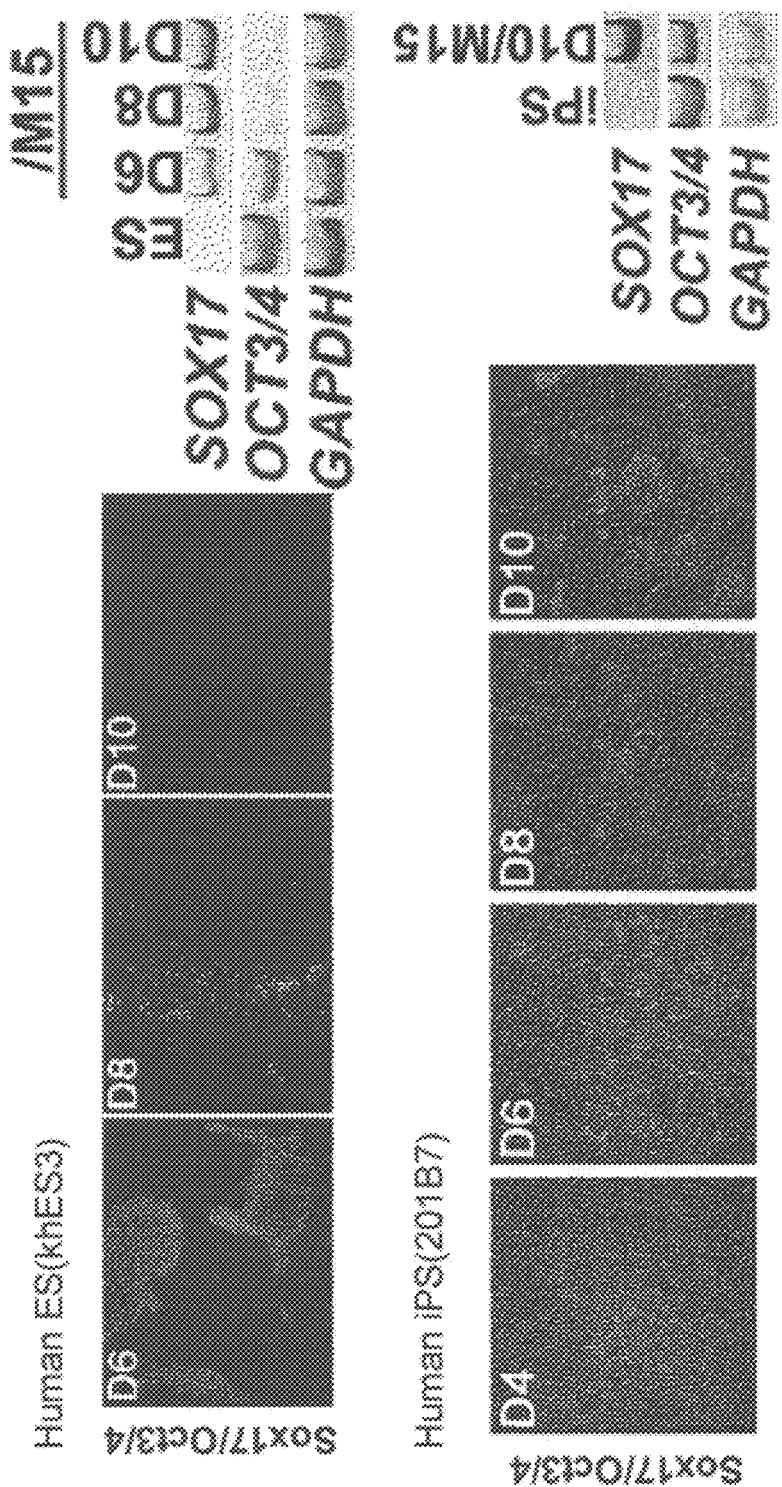
FIG. 1 shows confirmation of expression of Sox17 and Oct3/4 in a process of differentiating human ES cells and human iPS cells into endoderm cells, by immunofluorescent staining and RT-PCR. The upper stage shows the results of confirmation of expression of Sox17 and Oct3/4 of human ES cells on Day 6, Day 8 and Day 10 of culturing, by immunofluorescent staining (expression of Sox17 (red) and expression of Oct3/4 (green), left photograph) and RT-PCR (expression of Sox17 and Oct3/4, right photograph). The lower stage shows confirmation of expression of Sox17 and Oct3/4 of human iPS cells on Day 4, Day 6, Day 8 and Day 10 of culturing, by immunofluorescent staining (expression of Sox17 (red) and expression of Oct3/4 (green), left photograph), and of expression of Sox17 and Oct3/4 thereof on Day 10 of culturing, by RT-PCR (right photograph).

"Pluripotent stem cells" used in the present invention mean cells which have self-replication potential and can be cultured in vitro, and have pluripotency of being capable of differentiating into cells constituting an individual. Specifically mentioned are embryonic stem cells (ES cells), fetal primordial germ cell-derived pluripotent stem cells (GS cells), somatic cell-derived induced pluripotent stem cells (iPS cells) and the like, and particularly preferably used in the present invention are iPS cells or ES cells, and human iPS cells and human ES cells are particularly preferable.

The ES cells used in the present invention may advantageously be mammal-derived ES cells, and the kind and acquisition method thereof and the like are not particularly restricted. Examples of the mammal include mouse, rat, guinea pig, hamster, rabbit, cat, dog, sheep, cow, horse, goat, monkey or human, and the like, and preferable is mouse or human, further preferable is human.

For obtaining ES cells, a fertilized ovum in the blastocyst-stage is cultured together with feeder cells, and cells derived from the proliferated inner cell mass are discretely separated, further, transferred, this operation is repeated and finally a cell line can be attained, in a general way. As described above, ES cells are often obtained from a fertilized ovum, however, can also be obtained from other sources than a fertilized ovum, for example, fat tissue, placenta and testicular cells, and any ES cells are included in the present invention.

iPS cells (induced pluripotent stem cells) means cells which have acquired pluripotency, and are cells which have acquired the pluripotency equivalent to ES cells by introducing several transcription factor (pluripotent factor) genes imparting pluripotency to a somatic cell (for example, fibroblast and the like). As the "pluripotent factor", a lot of factors are reported, and examples thereof include, but not particularly limited to, Oct family (for example, Oct3/4), Sox family (for example, Sox2, Sox1, Sox3, Sox15 and Sox17 and the like), Klf family (for example, Klf4, Klf2 and the like), Myc family (for example, c-Myc, N-Myc, L-Myc and the like), Nanog, LIN28 and the like. There are a lot of reports on the iPS cell establishing method, and these can be used as a reference (for example, Takahashi et al., Cell 2006, 126: 663-676; Okita et al., Nature 2007, 448:313-317; Wernig et al., Nature 2007, 448:318-324; Maherali et al., Cell Stem Cell 2007, 1: 55-70; Park et al., Nature 2007, 451: 141-146; Nakagawa et al., Nat Biotechnol 2008, 26:101-106; Wernig et al., Cell Stem Cell 2008, 10:10-12; Yu et al., Science 2007, 318:1917-1920; Takahashi et al., Cell 2007, 131:861-872; Stadtfeld et al., Science 2008 322:945-949, and the like).

"Undifferentiated cells" used in the present invention denote cells having pluripotency, and in the context, denote cells which manifest no induction of differentiation even after a treatment to induce differentiation of pluripotent stem cells such as ES cells and iPS cells, and continuously have pluripotency.

Culturing of mammal-derived ES cells can be carried out by an ordinary method. For example, mouse embryonic fibroblasts (MEF cells) are used as feeder cells, and can be maintained using a culture medium containing leukemia inhibitory factor, KSR (knockout serum replacement), fetal bovine serum (FBS), non-essential amino acid, L-glutamine, pyruvic acid, penicillin, streptomycin and β-mercaptoethanol added, for example, a DMEM culture medium.

Culturing of iPS cells can also be carried out by an ordinary method. For example, MEF cells are used as feeder cells, and can be maintained using a culture medium containing bFGF, KSR (knockout serum replacement), non-essential amino acid, L-glutamine, penicillin, streptomycin and β-mercaptoethanol added, for example, a DMEM/F12 culture medium.

The system for induction of differentiation of pluripotent stem cells such as ES cells or iPS cells in the present invention includes any of a culture system containing feeder cells and a feeder free culture system. Examples of the feeder cells include, but not limited to, mmcM15 cells. Examples of the feeder free culture system include, but not limited to, sBM (synthesized Basement Membrane substratum).

"Differentiation" or "induction of differentiation" of pluripotent stem cells used in the present invention is used to denote induction of differentiation into any of endoderm, mesoderm or ectoderm cells, and further, also used to denote differentiation of them into any body part or organ cells constituting a living body.

The culture medium used in the culture method of the present invention can be prepared by using a culture medium used for culturing of animal cells as a basal culture medium. The basal culture medium includes, for example, BME culture medium, BGjB culture medium, CMRL 1066 culture medium, Glasgow MEM culture medium, Improved MEM culture medium, IMDM culture medium, Medium 199 culture medium, Eagles MEM culture medium, αMEM culture medium, DMEM culture medium, Ham's culture medium, RPMI 1640 culture medium, Fischer's and mixed culture media thereof and the like, and is not particularly restricted providing it can be used for culturing of animal cells.

The culture medium used in the culture method of the present invention can be a serum-containing culture medium or a serum-free culture medium, and the serum-free culture medium is preferable from the standpoint of securing safety of cell transplantation by exclusion of heterogeneous components. Here, the serum-free culture medium denotes a culture medium not containing a non-adjusted or unrefined serum, and a culture medium containing a purified blood-derived component or animal tissue-derived component (for example, growth factor) mixed is regarded as the serum-free culture medium. Examples of such a serum-free culture medium include, but not limited to, a serum-free culture medium containing a suitable amount (for example, 1-20%) of commercially available KSR added, a serum-free culture medium containing insulin and transferrin added, a culture medium containing a cell-derived factor added, and the like.

The culture medium of the present invention may contain or may not contain a serum replacement. The serum replacement can be, for example, albumin (for example, lipid-rich albumin), transferrin, fatty acid, insulin, collagen precursor, trace element, 2-mercaptoethanol or 3'-thiol glycerol, or those appropriately containing equivalents thereof and the like. Such a serum replacement can be prepared, for example, by a method described in International Publication WO 93/30679, and commercially available products can also be used. Examples of such commercially available serum replacements include the above-described KSR.

Further, the culture medium of the present invention can contain any components such as fatty acids or lipids, amino acids (for example, non-essential amino acids), vitamins, growth factors, cytokines, antioxidants, 2-mercaptoethanol, pyruvic acid, buffering agents, inorganic salts and the like. This is not applied when a culture medium is deprived of a specific amino acid according to the present invention.

In the present invention, undifferentiated cells can be reduced or removed by depriving a culture medium of a specific amino acid in differentiating pluripotent stem cells such as ES cells and iPS cells, and as a result, differentiation induction efficiency can be improved.

In general, amino acids are classified into essential amino acids (Thr, Met, Val, Leu, Ile, Phe, Trp, Lys, His) and non-essential amino acids (Gly, Ala, Ser, Cys, Gln, Asn, Asp, Tyr, Arg, Pro). Cys and Tyr among non-essential amino acids, however, are defined as a semi-essential amino acid since they need as a precursor amino acid Met and Phe as an essential amino acid. Arg can be defined as a semi-essential amino acid in undifferentiated cells since arginine synthetase shows low activity in undifferentiated cells (fetus/newborn). In the present invention and in the present specification, Cys, Tyr and Arg are called a semi-essential amino acid.

"Amino acid-deprived culture medium (hereinafter, referred to as "δ (amino acid-deprived) culture medium" in some cases)" used in the present invention denotes a differentiation culture medium, which does not contain a specific amino acid, can reduce undifferentiated pluripotent stem cells or enhance differentiation induction efficiency. The differentiation culture medium is not particularly restricted, and when differentiation into, for example, digestive tract, liver, pancreas and the like is desired, an endoderm differentiation culture medium not containing a specific amino acid is used, when differentiation into, for example, body cavity, blood vessel, heart and the like is desired, a mesoderm differentiation culture medium not containing a specific amino acid is used, and when differentiation into, for example, skin and nerve is desired, an ectoderm differentiation culture medium not containing a specific amino acid is used. Additionally, culture media inducing differentiation into specific organ cells, for example, a liver differentiation culture medium and a pancreas differentiation culture medium also correspond to "amino acid-deprived culture medium" called in the present invention providing that they do not contain a specific amino acid and can reduce undifferentiated pluripotent stem cells or enhance differentiation induction efficiency. "Amino acid-deprived culture medium" called in the present invention includes an endoderm differentiation culture medium, a mesoderm differentiation culture medium and an ectoderm differentiation culture medium not containing a specific amino acid, and an endoderm differentiation culture medium not containing a specific amino acid is preferable.

The specific amino acid not contained in "amino acid-deprived culture medium" in the present invention includes any one of methionine, leucine, cysteine, tyrosine and arginine, or an amino acid group containing a combination of two or more of them, or all of them in combination. A differentiation culture medium which does not contain at least one of the above-described amino acids can reduce undifferentiated pluripotent stem cells or enhance differentiation induction efficiency, and a differentiation culture medium which does not contain at least methionine is particularly preferable.

In other words, a differentiation culture medium contains, in general, all essential amino acids and non-essential amino acids excluding alanine, however, "amino acid-deprived culture medium" of the present invention is a differentiation culture medium which does not contain at least one amino acid selected from the group consisting of methionine and leucine as an essential amino acid and cysteine, tyrosine and arginine as a semi-essential amino acid.

In the present specification, "differentiation culture medium" and "differentiation inducing culture medium" represent mutually the same meaning and can be exchanged mutually.

"Containing as an amino acid at least threonine, valine, isoleucine, phenylalanine, tryptophan, lysine and histidine as an essential amino acid and not containing at least one amino acid selected from the group consisting of methionine, leucine, cysteine, tyrosine and arginine in the culture medium" means that the culture medium contains at least the above-described eight essential amino acids and can further contain other any amino acids, but at least one amino acid selected from the group consisting of methionine, leucine, cysteine, tyrosine and arginine or an amino acid group combining two or more of them is not contained in the culture medium. Examples thereof include a culture medium which contains the above-described eleven amino acids other than methionine and does not contain methionine, and a culture medium further containing non-essential amino acids.

"Does not contain an amino acid in the amino acid-deprived culture medium" in the present invention includes cases containing a trace amount of a specific amino acid, in addition to cases not containing a specific amino acid at all. The case containing a trace amount includes cases in which undifferentiated pluripotent stem cells can be reduced or removed or differentiation induction efficiency can be enhanced in differentiation since a specific amino acid is contained only at low concentration. More specifically, "does not contain an amino acid in the amino acid-deprived culture medium" in the present invention means that a differentiation culture medium contains any specific amino acid in an amount of 20 µM or less, preferably 10 µM or less, further preferably 1 µM or less, most preferably 0.1 µM or less, in addition to a case of no inclusion at all.

In the present invention, pluripotent stem cells are cultured in "amino acid-deprived culture medium" according to the present invention for at least 5 hours, preferably at least 1 day, further preferably at least 2 days. The period of culturing in "amino acid-deprived culture medium" according to the present invention is preferably 4 days or less, particularly preferably 2 days or less. If pluripotent stem cells are cultured in "amino acid-deprived culture medium" according to the present invention in all of the culture period, for example, on all of Days 0 to 10 in the initial period of differentiation induction, growth of cells is prevented and cells cannot grow.

In the present invention, it is preferable that pluripotent stem cells are cultured in a differentiation culture medium containing essential amino acids and semi-essential amino acids, then, in "amino acid-deprived culture medium" according to the present invention.

In induction of differentiation of pluripotent stem cells, the period of culturing pluripotent stem cells in "amino acid-deprived culture medium" according to the present invention is not particularly restricted, and the initial period of differentiation induction (period of differentiation into endoderm, mesoderm or ectoderm cells) or the late period of differentiation induction (period of differentiation of endoderm, mesoderm or ectoderm into various cells) may be permissible providing undifferentiated pluripotent stem cells can be reduced or differentiation induction efficiency can be enhanced, and preferable is the period of differentiation into endoderm, mesoderm or ectoderm cells, further preferable is the latter half period of the culturing period for differentiating pluripotent stem cells into endoderm, mesoderm or ectoderm cells, in other words, a period directly before formation of endoderm, mesoderm or ectoderm cells or a period in which formation thereof can be confirmed.

In the case of differentiation of human ES cells and human iPS cells into hepatocytes or pancreatic cells, the initial period of induction of differentiating ES cells/iPS cells into endoderm cells is preferable, and further preferable is the final period of induction of differentiation into endoderm cells, for example, a period of several days during Days 4 to 10 of culturing, for example, a period of Days 4 to 6 of culturing or Days 8 to 10 of culturing, most preferably a period of Days 8 to 10 of culturing.

In the case of transplantation of differentiated cells, undifferentiated pluripotent stem cells can be reduced or removed from transplanted cells by culturing in "amino acid-deprived culture medium" according to the present invention directly before transplantation.

In induction of differentiation of pluripotent stem cells into hepatocytes or pancreatic cells according to the present invention, pluripotent stem cells can be cultured in "amino acid-deprived culture medium" according to the present invention before culturing in a differentiation culture medium containing proline added, thereby an improvement in differentiation induction efficiency can be expected.

The amount of proline added to a differentiation culture medium is 1.0 mM or more and 100 mM or less, preferably 1.0 mM or more and 50 mM or less, further preferably 1.0 mM or more and 10 mM or less.

EXAMPLES

The present invention will be specifically illustrated by examples below, but the present invention is not limited to the following examples.

(A) MATERIAL AND METHOD (1) Maintenance and Culture of Human ES Cells

Human ES cells (khES3) (Biochem Biophys Res Commun. 2006, 345(3), 926-32) provided from Dr. Nakatsuji and Dr. Suemori (Kyoto University) were used according to Guideline on the Utilization of Human Embryonic Stem Cells (published by Ministry of Education, Culture, Sports, Science and Technology).

Undifferentiated human ES cells were cultured under conditions of 37° C. and 5% $CO_2$ on a feeder layer of mouse embryonic fibroblasts (MEF) as supporting cells in Knockout Dulbecco's Modified Eagle culture medium (DMEM/F12) (Invitrogen) containing 20% KSR (knockout serum replacement; Invitrogen), 100 μM non-essential amino acid (NEAA; GIBCO), 2 mM L-glutamine (Nacalai Tesque), 50 units/ml penicillin and 50 μg/ml streptomycin (Nacalai Tesque), 100 μM β-mercaptoethanol (Sigma) and 5 ng/ml bFGF (bovine fibroblast growth factor) added. For passage of human ES cells, human ES cell colonies were separated from the supporting cell layer by treating with 0.25% trypsin and 0.1 mg/ml collagenase IV at 37° C. for 5 minutes in PBS containing 20% KSR and 1 mM $CaCl_2$, thereafter, a culture medium was added, and the ES cell mass was made into small pieces by gently sucking by a pipette several times (5 to 20 cells). Passage was carried out at a division ratio of 1:2.

(2) Maintenance and Culture of Human iPS Cells

Human iPS cell line (201B7) provided from Dr. Takahashi (Takahashi K et al. Cell. 131(5): 861-72, 2007) was used. Human iPS cells (Toe cell line) (JCRB1338) sub-divided from those deposited by Dr. Umezawa Akihiro (National Center for Child Health and Development, Laboratory) et al. with an independent administrative institution, National Institute of Biomedical Innovation were used. Here, human iPS cells used were 201B7 unless otherwise stated in descriptions in the following examples.

Also undifferentiated human iPS cells were maintained and cultured in the same manner as for human ES cells.

(3) Preparation of Feeder Cells (mmcM15 Cells)

mmcM15 cells (mouse mesonephros) are registered on Cell Bank (CAMR Center for Applied Microbiology & Research (ECACC, Salisbury, Wiltshire)) under a registration number of ECACC95102517. M15 cells are available according to the description of a literature (Larsson, S. H., Charlieu, J. P., Miyagawa, K., et al. (1995). Subnuclear localization of WT1 in splicing or transcription factor domains is regulated by alternative splicing. Cell 81, 391-401).

(4) Immunocytochemistry Test (Immunofluorescent Staining)

In performing a whole mount immunohistochemistry test, ES cells or iPS cells were placed on Nunc Theranox Colerslips 24-well type (Nunc). Cells were fixed at room temperature for 20 minutes in 4% paraformaldehyde, and washed sufficiently with 0.1% Tween-containing phosphate buffered saline (PBS-T). In PBS containing 1% TritonX-100, the cells were infiltrated at room for 10 minutes, and incubated for 1 hour in a blocking solution (×5 Blocking One, Nacalai Tesque), then, primary antibodies in the blocking solution were added to the sample, and incubated at 4° C. overnight. The sample was washed sufficiently with PBS-T, and mounted with PermaFluor Aqueous Mounting culture medium (IMMUNON). A confocal image was obtained using Leica Spectral Confocal Scanning System, TCS-SP2 (Leica).

Antibodies used for detection are as described below. Rabbitanti-α-fetoprotein (AFP, Dako), goat anti-albumin (Sigma), rabbit anti-Pdx1 (Chemicon), mouse anti-Oct3/4 (Santa Cruz), goat anti-Sox17 (R&D). As secondary antibodies, Alexa568-labeled goat anti-rabbit antibody and donkey anti-goat antibody, and Alexa488-labeled goat anti-mouse antibody and goat anti-rabbit antibody, donkey anti-goat antibody (Molecular Probes) were used. Cells were counter-stained with DAPI (Roche). The numbers of Sox17 and Oct3/4 positive cells were quantified using ImageXpress (Molecular Devices Corporation).

(5) Indocyanine Green Test

Indocyanine green (ICG; Daiichi Sankyo Company, Limited) was diluted with a culture medium, to give a final concentration of 1 mg/ml. An ICG test solution was added to differentiated iPS cells, and incubated for 30 minutes under 37° C. and 5% $CO_2$. Thereafter, the ICG-containing culture medium was removed, and washed with HBSS three times. Cell uptake of ICG was observed by an electron microscope for 24 hours after the ICG treatment.

(6) Albumin Secretion Test

The culture medium was changed to a fresh culture medium, and cultured for 24 hours or 48 hours, then, the culture supernatant was collected. Human albumin secreted into the culture supernatant was measured by ELISA Quantitation kit (Bethyl Laboratories).

(7) Measurement of CYP Activity

For confirmation of cytochrome P450 activity, P450-Gro (trademark) CYP3A4 Assay with Luciferin-IPA (Promega) was used. On Day 30 of induction of differentiation, the culture medium was changed to a culture medium containing a suitable luminescent CYP substrate. Cells were cultured at 37° C. for 3 hours according to the manufacturer instruction for use, then, the culture supernatant was mixed with an equal amount of a detection reagent.

(8) PAS Staining (Periodic Acid Schiff Staining)

For detection of glycogen storage in differentiated cells, PAS staining kit (Muto Pure Chemicals Co., Ltd.) was used. Cells cultured for 30 days were fixed in 3.3% formalin for 10 minutes, then, stained according to the manufacturer instruction for use.

(9) Real Time PCR Analysis

Using RNeasy mini-kit (Qiagen), RNA was extracted from ES cells, then, RNA was treated with a DNA degrading enzyme (Qiagen). For investigating the RT reaction, 3 μg of RNA was reverse-transcribed using MMLV reverse transcriptase (Toyobo Co., Ltd.) and oligo dT primer (Toyobo Co., Ltd.). One micro liter (1 μl) of 5-fold diluted cDNA (1% of RT product) was used for PCR analysis. Using quantitative RT-PCR, expression of a liver differentiation marker (AFP, Albumin) in each amino acid culture medium was quantified, and compared with time.

(B) EXAMPLES

Reference Example 1

Differentiation of Human ES Cells and Human iPS Cells into Endoderm Cells

Human ES cells (KhES3 strain) and human iPS cells (201B7) maintained and cultured according to Material and Method (1) were differentiated into endoderm cells.

On the day before seeding human ES cells/iPS cells, mmcM15 cells were previously seeded on a gelatin-coated 96-well plate at a cell density of $5.0 \times 10^4$ cells/well (mmcM15 plate).

Human ES cells/iPS cells were cultured for 1 day in a culture medium prepared by adding Rock inhibitor (Y27632; 10 μM, Wako Pure Chemical Industries, Ltd.) and 5 ng/ml bFGF to ReproStem culture medium (ReproCell), prior to induction of differentiation.

For induction of differentiation, human ES cells/iPS cells were peeled from a culture dish using 0.25% trypsin EDTA (Invitrogen), and seeded on an mmcM15 cell plate treated with mitomycin C at a cell concentration of $1 \times 10^4$ cells/well.

ES/iPS cells were washed once with PBS on the next day after seeding, then, transferred to a differentiation culture medium. As the differentiation culture medium for differentiation into endoderm cells, PRMI 1640 culture medium (Invitrogen) containing 100 ng/ml activin (R&D Systems), B27 culture medium additive (Invitrogen), 50 units/ml penicillin and 50 µg/ml streptomycin (Nacalai Tesque), 2 mM L-glutamine (Nacalai Tesque) and 100 µM β-mercaptoethanol (Sigma) was used. The culture medium was changed to a new culture medium every other day.

Human ES cells/iPS cells were cultured for 10 days in a differentiation culture medium. The human ES cells were subjected to immunofluorescent staining with an anti-Sox17 antibody and an Oct3/4 antibody on Day 6, Day 8 and Day 10 of culturing after transferring to the differentiation culture medium. The human iPS cells were subjected to immunofluorescent staining with Sox17 and Oct3/4 on Day 4, Day 6, Day 8 and Day 10 of culturing.

The results are shown in FIG. 1. As a result of immunofluorescent staining, Sox17-positive (red) endoderm cells could be confirmed on Day 10 of culturing, both for human ES cells and human iPS cells.

RT-PCR was conducted for expressions of Sox17 and Oct3/4 according to Material and Method (9) (expression of GAPDH was confirmed as control). The results are shown in FIG. 1. As a result of RT-PCR, expression of an undifferentiated cell marker Oct3/4 disappeared in human ES cells on Day 10 of culturing, while in human iPS cells, expression still remained. This fact suggests that human iPS cell line (201B7) shows resistance against differentiation into endoderm cells as compared with human ES cell line (KhES3 strain).

Reference Example 2

Differentiation of Human ES Cells and Human iPS Cells into Liver Cells

In the same manner as in Reference Example 1, cells were cultured for 10 days in an endoderm differentiation culture medium, then, the culture medium was changed to a liver differentiation culture medium. As the liver differentiation culture medium, DMEM culture medium (Invitrogen) containing 1 µM dexamethasone (Sigma), 10µ/ml human recombinant HGF (Peprotech), 0.5% DMSO (Sigma), 0.5 mM nicotinamide (Sigma), 0.2 mM ascorbic acid (Sigma), 10% KSR, 2000 mg/l glucose, 50 units/ml penicillin and 50 µg/ml streptomycin (Nacalai Tesque), 2 mM L-glutamine (Nacalai Tesque), and 100 µM β-mercaptoethanol (Sigma) was used. The culture medium was changed to a new culture medium every other day until Day 29.

Figure 2:
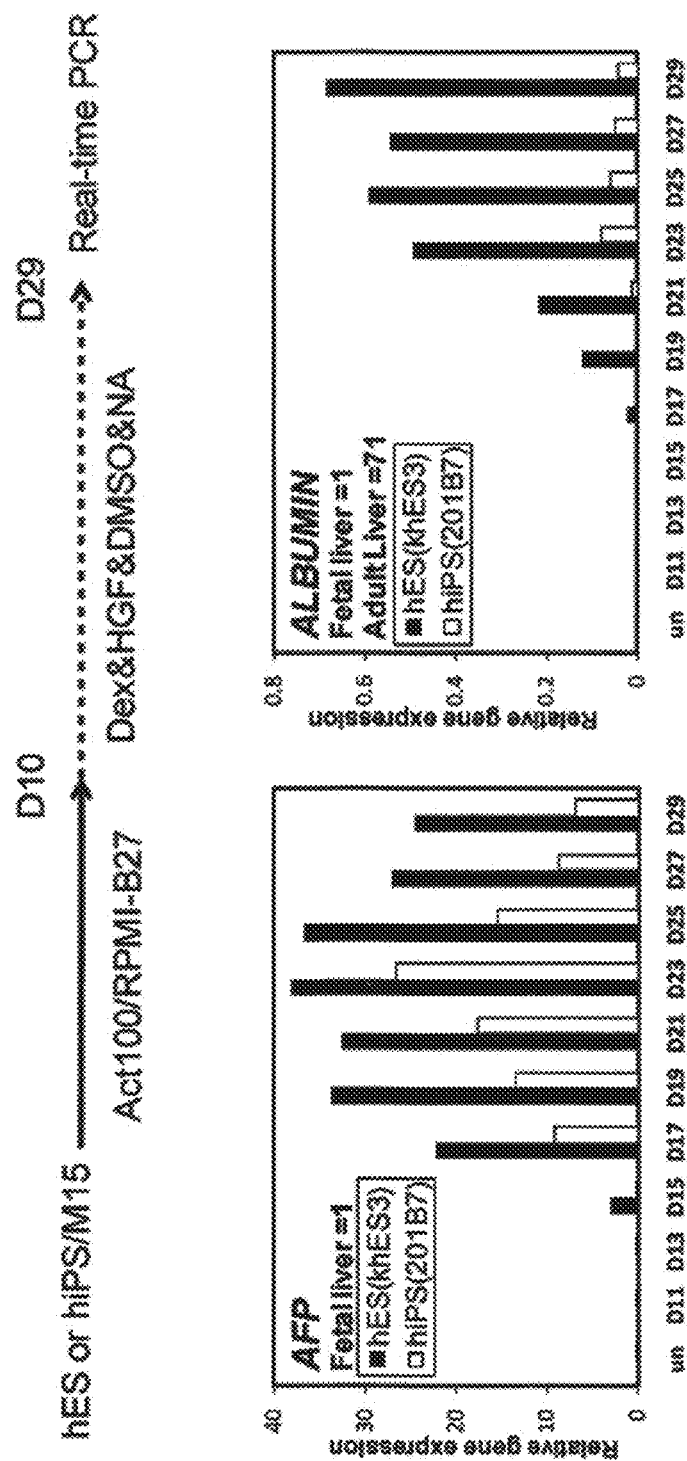
FIG. 2 shows confirmation of expression of AFP (α-fetoprotein) and albumin in a process of differentiating human ES cells and human iPS cells into liver cells, by RT-PCR. The left figure shows observation of expression of AFP, and the right figure shows observation of expression of albumin.

RT-PCT was conducted for expressions of AFP as an immature hepatocyte marker and albumin as a mature hepatocyte marker according to Material and Method (9). The results are shown in FIG. 2. The black bar represents the expression amount of human ES cells and the white bar represents the expression amount of human iPS cells.

As a result, for AFP, the expression amount of iPS cell line was lower than that of ES cell line in all culturing periods. Further, for albumin, iPS cells showed remarkably lower expression as compared with ES cells. These results suggest that human iPS cell line (201B7) shows resistance not only against differentiation into endoderm cells but also against differentiation into liver cells, as compared with human ES cell line (KhES3 strain).

Example 3: Influence of Amino Acid on Differentiation into Endoderm Cells Using Human iPS Cells Differentiation of human iPS cells into endoderm cells was induced using endoderm differentiation culture media deprived of one amino acid for each culture medium. For induction of differentiation into endoderm cells, an endoderm differentiation inducing method using mmcM15 cells was used (see, non-patent document 6).

As the culture medium, the following media were used depending on the culturing period. From initiation of culturing (Day 0) until Day 6 or Day 8 of culturing, PRMI 1640 culture medium (Invitrogen) containing 50 units/ml penicillin and 50 µg/ml streptomycin (GIBCO), 2 mM L-glutamine (GIBCO), 100 µM β-mercaptoethanol (Sigma), non-essential amino acid (GIBCO), 100 ng/ml activin (R&D Systems) and B27 culture medium additive (Invitrogen) added was used as an endoderm differentiation culture medium.

From Day 6 or Day 8 until Day 10, amino acid-deprived culture media obtained by removing one amino acid from PRMI 1640 culture medium containing 50 units/ml penicillin and 50 µg/ml streptomycin, 2 mM L-glutamine, 100 µM β-mercaptoethanol, 100 ng/ml activin and B27 culture medium additive added, or a culture medium not deprived of an amino acid (control culture medium) was used as an endoderm differentiation culture medium.

Specifically, mmcM15 cells were seeded as supporting cells on a gelatin-coated 96-well plate. Human iPS cells were treated with Y27632 (10 µM) from 24 hours before seeding, and peeled using 0.25% trypsin. The peeled human iPS cells were seeded on mmcM15 cells at a cell concentration of $1 \times 10^4$ cells/well. The seeded human iPS cells were cultured for 24 hours under 37° C. and 5% $CO_2$ in ES culture medium (ReproStem, ReproCell) containing 10 µM Y27632 and 5 ng/ml bFGF added. After 24 hours, cells were washed once with PBS, then, the culture medium was changed to an endoderm differentiation culture medium (Day 0). Until Day 6 or Day 8 of culturing, the endoderm differentiation culture medium was changed every other day, and human iPS cells were cultured under 37° C. and 5% $CO_2$. On Day 6 or Day 8, the culture medium was changed to an amino acid-deprived culture medium or a control culture medium. Human iPS cells were cultured until Day 10 of culturing using an amino acid-deprived culture medium or a control culture medium. On Day 10, human iPS cells were subjected to immunofluorescent staining, and the proportions of positive cells for an endoderm differentiation marker (Sox17) and an undifferentiation marker (Oct3/4) were quantitatively analyzed. The proportion of the positive cells based on those stained with DAPI was calculated.

Figure 3:
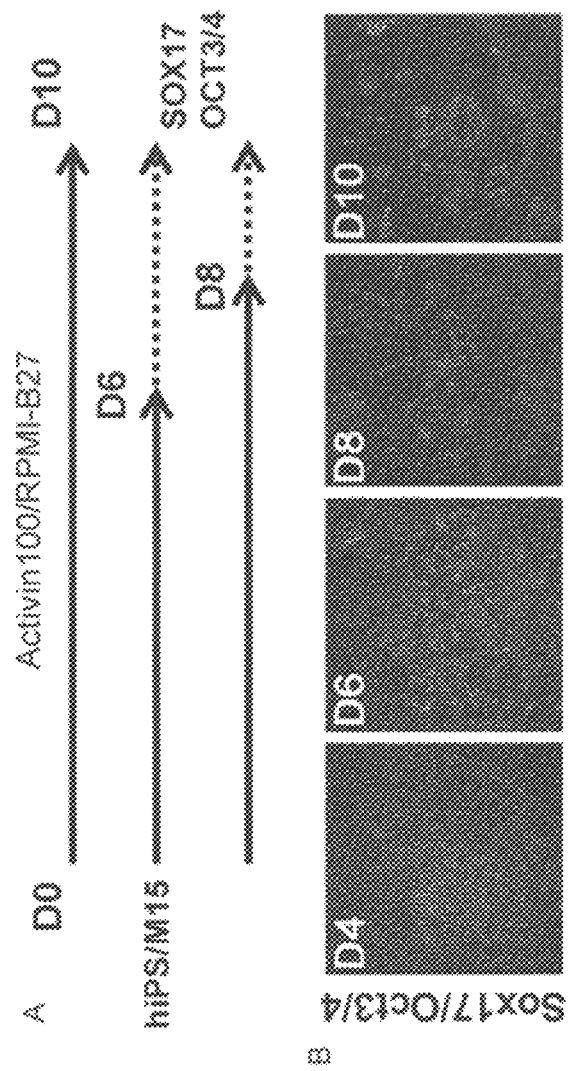
FIG. 3 shows the results of examination of an influence of an amino acid on differentiation into endoderm cells using human iPS cells.
Figure 4:
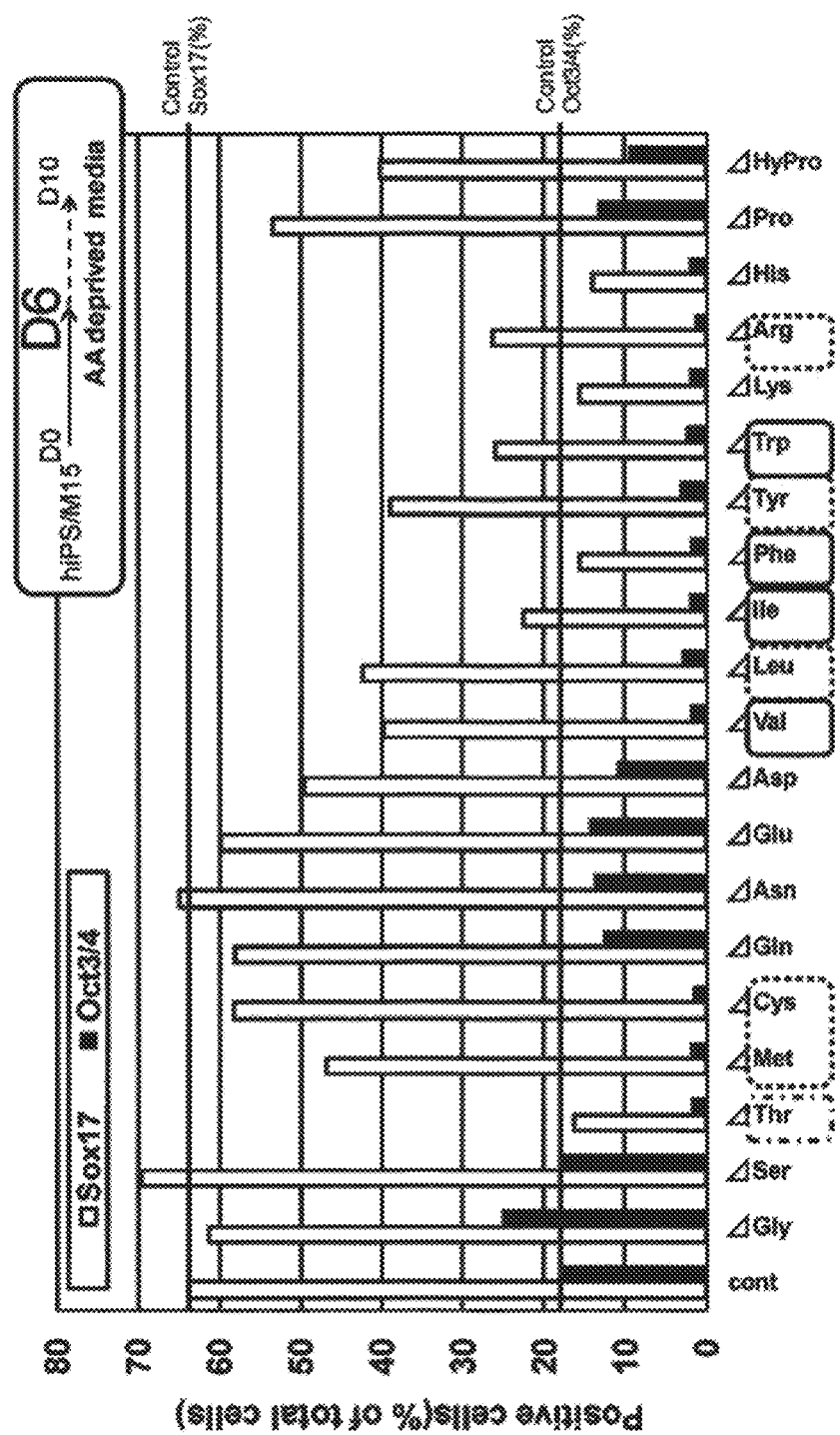
FIG. 4 shows the results of examination of an influence of an amino acid on differentiation into endoderm cells using human iPS cells. On Day 6, the culture medium was changed to an amino acid-deprived culture medium, and human iPS cells cultured until Day 10 were immunofluorescent-stained and the proportions of positive cells for the endoderm differentiation marker (Sox17) and the undifferentiation marker (Oct3/4) were quantitatively analyzed, the analyzed results being shown in FIG. 4 (the proportion of the positive cells based on those stained with DAPI was calculated). X axis represents the kind of the deprived amino acid and Y axis represents the positive cell ratio (%).

FIG. 3A represents the culture schedule. The results of immunofluorescent staining in a control culture medium are shown in FIG. 3B The results of quantitative analysis of the proportions of positive cells for an endoderm differentiation marker (Sox17) and an undifferentiation marker (Oct3/4) are shown in FIG. 4. The proportion of the positive cells was compared between each amino acid-deprived culture medium and a control. X axis represents the kind of the deprived amino acid and Y axis represents the positive cell ratio (O). The black bar represents the result for Oct3/4 positive cells and the white bar represents the result for Sox17 positive cells.

Amino acid deprivation between Day 6 to Day 10 influenced the proportions of Oct3/4 positive cells and Sox17 positive cells. Deprivation of each of essential amino acids (Thr, Met, Val, Leu, Ile, Phe, Trp, Lys, His) and semi-essential amino acids (Cys, Tyr, Arg) decreased the Oct3/4 positive cell ratio. The SOX17 positive cell ratio did not increase in deprivation of any amino acids excluding Ser.

Example 4: Influence of Amino Acid Deprivation Between Day 8 and Day 10 on Differentiation of Human iPS Cells into Endoderm Cells In the same manner as in Example 3, an influence of amino acid deprivation between Day 8 and Day 10 on differentiation into endoderm cells was confirmed using human iPS cells. Here, human iPS cells were cultured in a usual culture medium until Day 8 (from Day 0 to Day 8) using an endoderm differentiation inducing method using mmcM15 cells, then, the culture medium was changed to an amino acid-deprived culture medium or a control culture medium and human iPS cells were cultured from Day 8 to Day 10.

Figure 5:
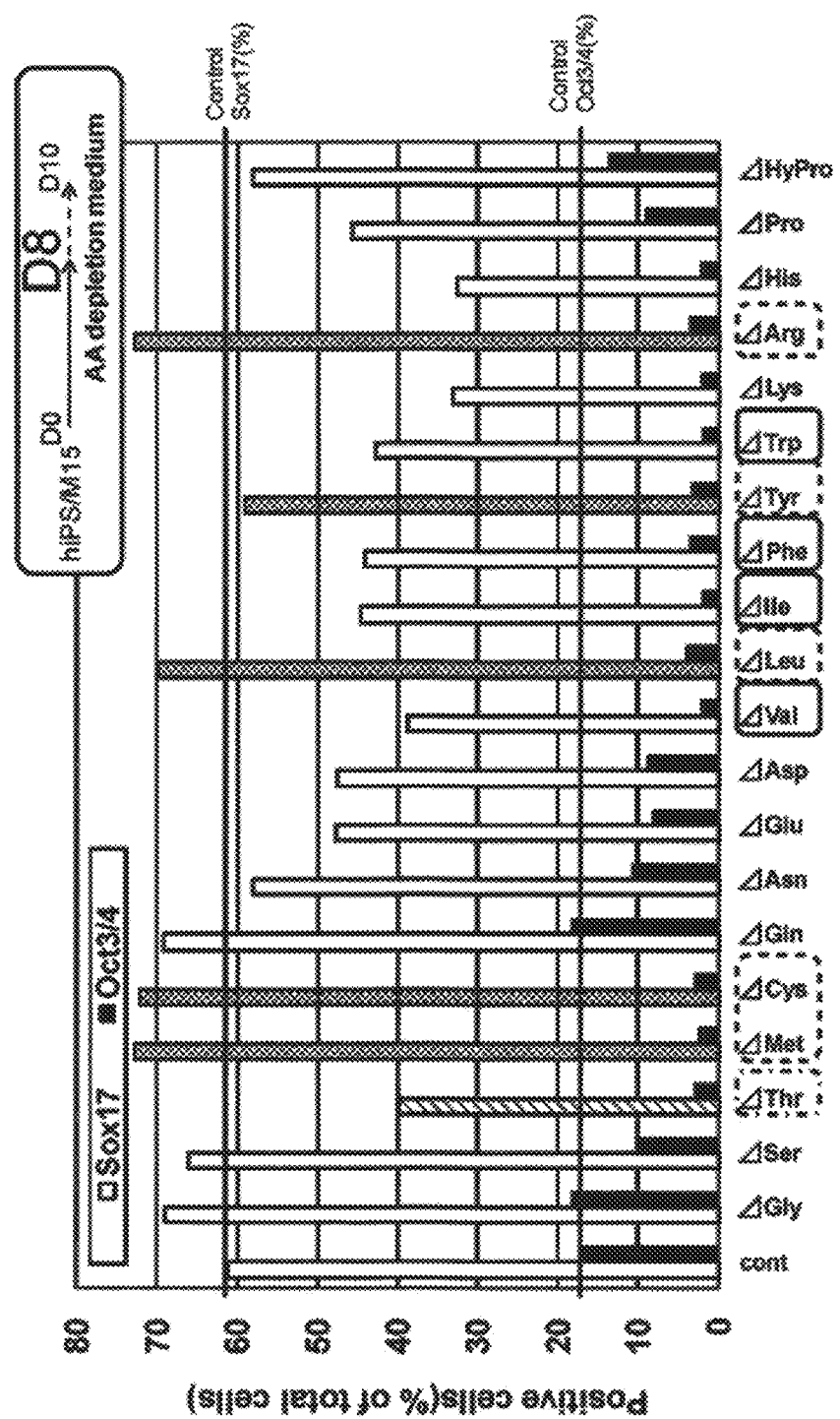
FIG. 5 shows the results of examination of an influence of an amino acid on differentiation into endoderm cells using human iPS cells. On Day 8, the culture medium was changed to an amino acid-deprived culture medium, and human iPS cells cultured until Day 10 were immunofluorescent-stained and the proportions of positive cells for the endoderm differentiation marker (Sox17) and the undifferentiation marker (Oct3/4) were quantitatively analyzed, the analyzed results being shown in FIG. 5 (the proportion of the positive cells based on those stained with DAPI was calculated). X axis represents the kind of the deprived amino acid and Y axis represents the positive cell ratio (%).

On Day 10, human iPS cells were subjected to immunofluorescent staining, and the proportions of Sox17 positive cells and Oct3/4 positive cells were quantified. The proportion of the positive cells was compared between each amino acid-deprived culture medium and a control culture medium. The results are shown in FIG. 5. X axis represents each deprived amino acid and Y axis represents the positive cell ratio (%). The black bar represents the result for Oct3/4 positive cells and the white bar represents the result for Sox17 positive cells.

Amino acid deprivation between Day 8 and Day 10 influenced the proportions Oct3/4 positive cells and Sox17 positive cells. In a Thr-deprived culture medium, which Thr had been reported as essential for survival of mouse ES cells in non-patent document 2, also the number of Sox17 positive cells decreased together with Oct3/4 positive cells, thus, this culture medium was not suitable as a selective culture medium (oblique line bar). Deprivation of each of essential amino acids (Thr, Met, Val, Leu, Ile, Phe, Trp, Lys, His) and semi-essential amino acids (Cys, Tyr, Arg) remarkably decreased the Oct3/4 positive cell ratio. Deprivation of Gly, Ser, Met, Cys, Gln, Leu or Arg increased the Sox17 positive cell ratio. Both a decrease in Oct3/4 and an increase in Sox17 were observed in culture media deprived of Met, Cys, Leu or Arg (dot bar), and a decrease in Oct3/4 was observed without change of Sox17 in a culture medium deprived of Tyr (dot bar).

Figure 6:
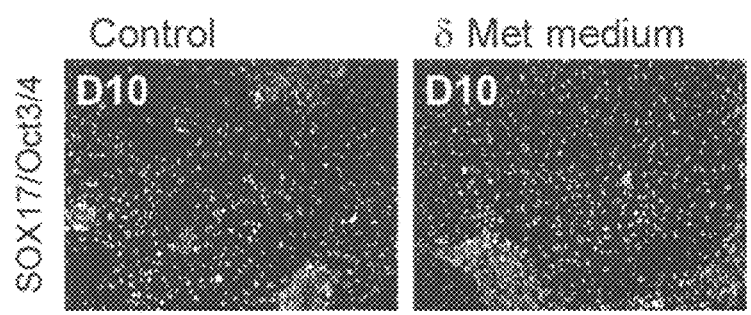
FIG. 6 shows the results of immunofluorescent staining of human iPS cells differentiated into endoderm cells using a methionine-deprived culture medium (δMet culture medium), with an anti-Sox17 antibody (red) and an anti-Oct3/4 antibody (green).

Human iPS cells were cultured in a methionine-deprived culture medium (δMet culture medium) to be differentiated into endoderm cells between Day 8 and Day 10 and the differentiated cells were subjected to immunofluorescent staining and the stained cells were shown in FIG. 6. In human iPS cells cultured using a control culture medium, Oct3/4 positive cells remain and are present together with Sox17 positive cells. While, in human iPS cells cultured using a methionine-deprived culture medium, stay of Oct3/4 positive cells is not recognized and Sox17 positive cells are present uniformly.

Example 5: Influence of Deprivation of Methionine Between Day 8 And Day 10 on Differentiation of Human iPS Cells into Hepatocytes For investigating an influence of a change in methionine concentration in a process of differentiation of human iPS cells into endoderm cells on differentiation of human iPS cells into hepatocytes, human iPS cells were treated in a methionine-deprived culture medium and a culture medium containing any concentration of methionine from Day 8 to Day 10, then, cultured in a liver differentiation culture medium, and a change of expression of AFP as a liver marker in this procedure was measured. The methionine addition concentration between Day 8 and Day 10 was 1, 0.1, 1.0, 5.0, 10.0, 20.0, 50.0, 100, 200 and 500 μM.

In the same manner as in Example 4, differentiation of human iPS cells into endoderm cells was induced until Day 8 using mmcM15 cells, and the culture medium was changed to a methionine-deprived culture medium and a culture medium containing any concentration of methionine during Day 8 to Day 10 and cultured under 37° C. and 5% $CO_2$ until Day 10.

Figure 7:
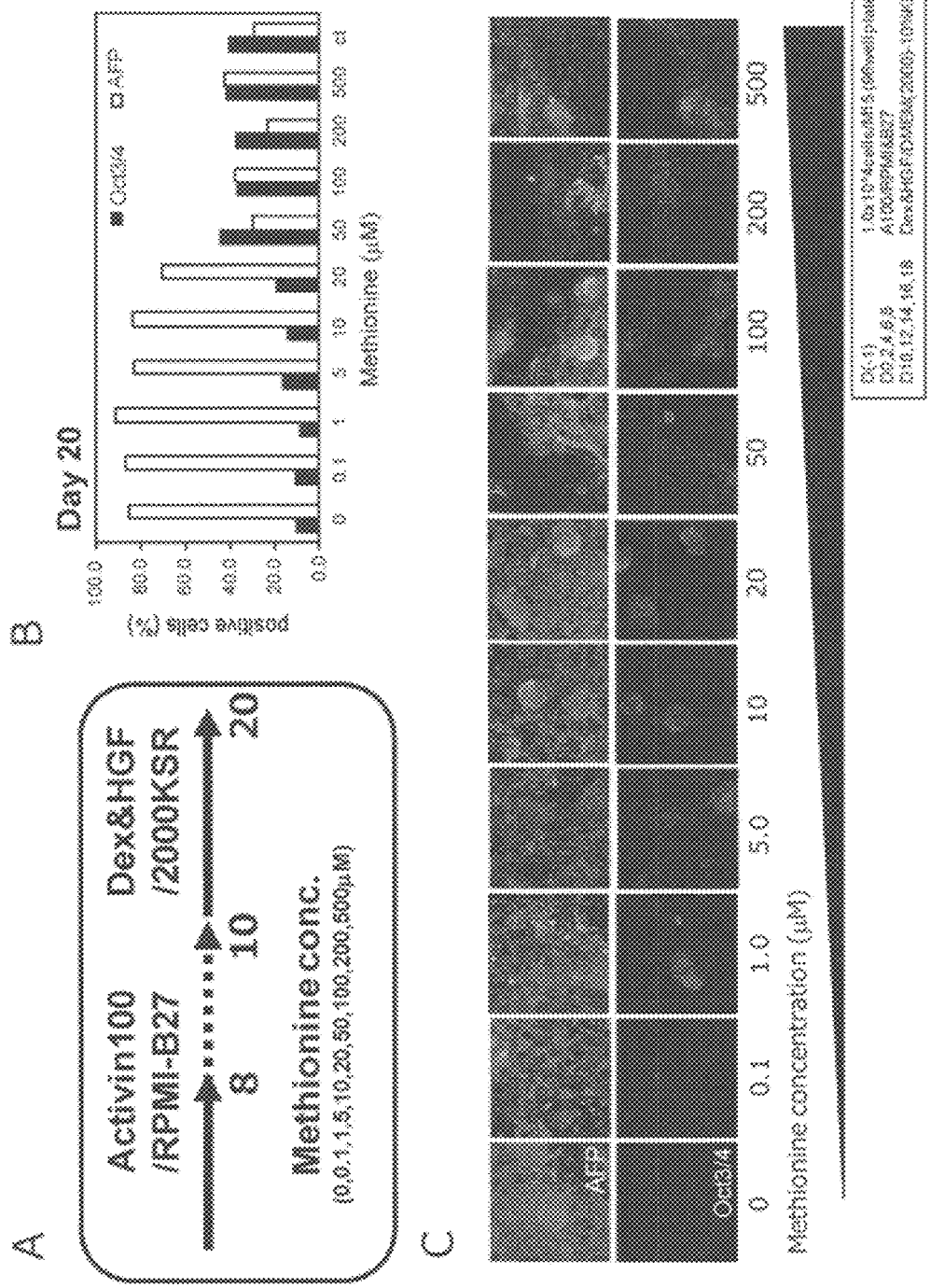
FIG. 7 shows the results of examination of an influence of a methionine-deprived endoderm differentiation culture medium on differentiation into liver cells using human iPS cells.

On Day 10, the culture medium was changed to a liver differentiation culture medium (MEME culture medium containing 10% KSR, 2000 mg/l D-glucose, 50 units/ml penicillin and 50 μg/ml streptomycin, 2 mM L-glutamine, 100 μM β-mercaptoethanol, 10μ/ml human recombinant HGF and 1 μM dexamethasone (hereinafter, referred to as "2000KSR-DMEM culture medium")), and cultured under 37° C. and 5% $CO_2$ until Day 20. During Day 10 to Day 20, the culture medium was changed every other day. On Day 20, human iPs cells were subjected to immunofluorescent staining, and the proportions of Oct3/4 positive cells and AFP positive cells were compared for every methionine concentration. The results are shown in FIG. 7.

The results of FIG. 7B taught the following fact. The proportion of Oct3/4 positive cells on Day 20 increased depending on the methionine concentration. The proportion of AFP positive cells decreased at methionine concentrations of 50 μM or more.

From FIG. 7C, the following fact was confirmed. The number of Oct3/4 positive cells on Day 20 increased depending on the methionine concentration. At methionine concentrations of 0 μM to 0.1 μM, the amount of remaining Oct3/4 positive cells was small and AFP positive cells are present uniformly. At methionine concentrations of 1 μM to 20 μM, the number of Oct3/4 positive cells increases slightly, however, a decrease in the number of AFP positive cells is not recognized. At methionine addition concentrations of 50 μM or more, a remarkable increase in the number of Oct3/4 positive cells and a remarkable decrease in the number of Sox17 positive cells are recognized.

Example 6: Influence of Deprivation of Methionine on Differentiation of Human iPS Cells into Hepatocytes In the same manner as in Example 4, differentiation of human iPS cells into endoderm cells was induced until Day 8 using mmcM15 cells, and from Day 8 to Day 10, the culture medium was changed to a methionine-deprived culture medium (δMet culture medium) or a control culture medium, and human iPS cells were cultured under 37° C. and 5% $CO_2$.

On Day 10, the culture medium was changed to a liver differentiation culture medium (2000KSR-DMEM culture medium), and human iPS cells were cultured under 37° C. and 5% $CO_2$ until Day 30. During Day 10 to Day 30, the culture medium was changed every other day.

Example 6-1

Figure 8:
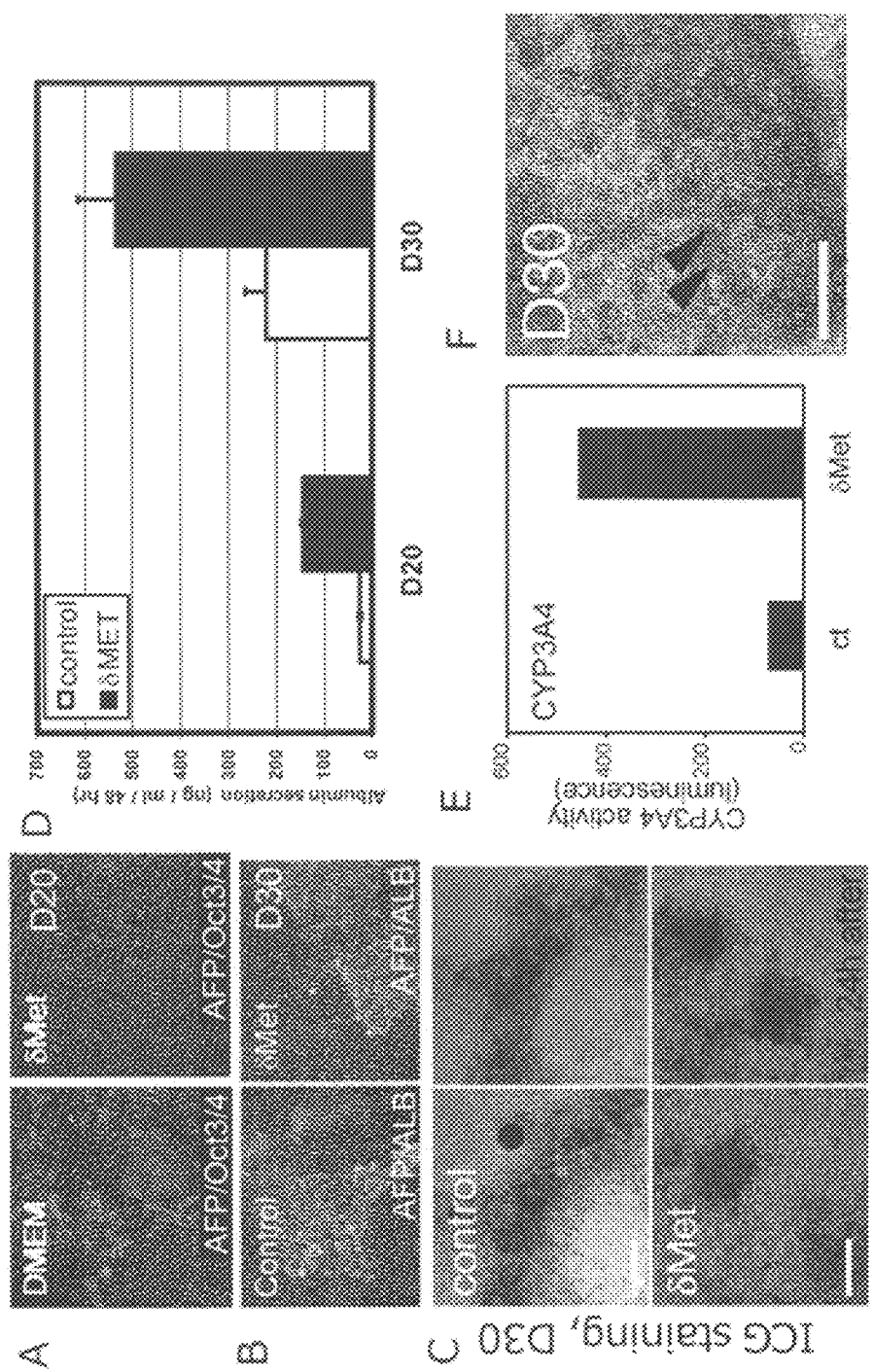
FIG. 8 shows the results of examination of various liver markers, in human iPS cells differentiated into liver cells in a methionine-deprived culture medium.

Human iPS cells cultured for 20 days were subjected to immunofluorescent staining with an anti-AFP antibody and an anti-Oct3/4 antibody. The results are shown in FIG. 8A. In human iPS cells cultured using a control culture medium, stay of Oct3/4 positive cells was recognized on Day 20, while in human IFS cells cultured using the δMet culture medium, stay of Oct3/4 positive cells was not recognized on Day 20.

Example 6-2

Human iPS cells cultured for 30 days were subjected to immunofluorescent staining with an anti-AFP antibody and an anti-albumin antibody. The results are shown in FIG. 8B. Albumin positive cells could be recognized on Day 30 also in human iPS cells cultured using the δMet culture medium, like human IFS cells cultured using a control culture medium.

Example 6-3

A test of uptake-excretion of indocyanine green (ICG) on Day 30 was carried out according to Material and Method (5). The results are shown in FIG. 8C.

The upper stage represents human iPS cells (Day 30) cultured in a liver differentiation culture medium after culturing in a control culture medium, and the lower stage represents human iPS cells (Day 30) cultured in a liver differentiation culture medium after culturing in the δMet culture medium. The left column represents the result at 0 hour after treatment with ICG and the right column represents the result at 24 hours after treatment with ICG.

Uptake of ICG and excretion thereof after 24 hours were recognized in both human iPS cells cultured in a control culture medium and human iPS cells cultured in the δMet culture medium.

Example 6-4

The albumin secretion amount was measured on Day 20 and Day 30 according to Material and Method (6). On Day 20 and Day 30, the albumin amount in a culture solution 48 hours after change of the culture medium was measured, and the albumin amount secreted in two days was quantified (n=4). The results are shown in FIG. 8D. Human iPS cells cultured in the δMet culture medium showed remarkably higher albumin secretion activity as compared with control.

Example 6-5

CYP3A4 activity on Day 30 was examined according to Material and Method (7). The results are shown in FIG. 8E. Human iPS cells cultured in the δMet culture medium showed higher CYP3A4 activity as compared with the control culture medium (ct).

Example 6-6

Human iPS cells cultured for 30 days were subjected to PAS staining according to Material and Method (8). The results are shown in FIG. 8F. In human iPS cells cultured in the δMet culture medium, PAS positive cells were present, and partially binuclear cells (arrow).

Example 7: Influence of Deprivation of Methionine During Day 8 to Day 10 on Differentiation of Human iPS Cells into Pancreatic Cells For investigating an influence of deprivation of methionine in a process of differentiation of human iPS cells into endoderm cells on differentiation of human iPS cells into pancreas cells, human iPS cells were treated in a control culture medium or a methionine-deprived culture medium on Day 8 to Day 10, then, cultured in a pancreas differentiation culture medium until Day 13, and expression of Pdx1 as a functional pancreas β cell marker was examined.

In the same manner as in Example 4, differentiation of human iPS cells into endoderm cells was induced until Day 8 using mmcM15 cells, and during Day 8 to Day 10, the culture medium was changed to a control culture medium or a methionine-deprived culture medium and human iPS cells were cultured under 37° C. and 5% $CO_2$ until Day 10.

On Day 10, human iPS cells were transferred into a pancreas differentiation culture medium (DMEM culture medium containing 2000 mg/l D-glucose, 50 units/ml penicillin and 50 µg/ml streptomycin (GIBCO), 2 mM L-glutamine (GIBCO), 100 µM β-mercaptoethanol (Sigma), non-essential amino acid (GIBCO), 1 µM retinoic acid, 50 ng/ml Fgf10 (Fibroblast growth factor-10), 0.25 µM KAAD-cyclopamine and B27 culture medium additive added). The culture medium was changed to a new culture medium every day during Day 10 to Day 13.

Figure 9:
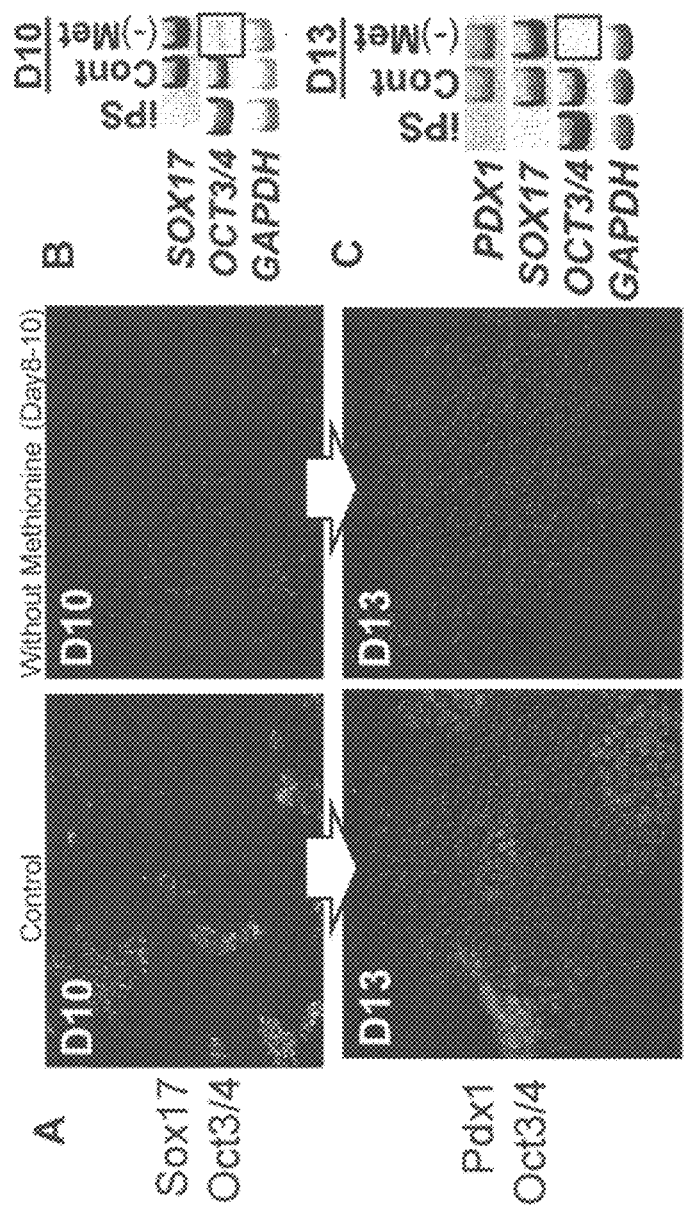
FIG. 9 represents the results of examination of an influence of methionine deprivation on Day 8 to Day 10 on differentiation of human iPS cells into pancreatic cells.

Human iPS cells on Day 10 were subjected to immunofluorescent staining with an anti-Oct3/4 antibody and an anti-Sox17 antibody and human iPS cells on Day 13 were subjected to immunofluorescent staining with an anti-Oct3/4 antibody and an anti-Pdx1 antibody. The results are shown in FIG. 9A.

RT-PCR was carried out for expressions of Sox17, Oct3/4 and Pdx1 (expression of GAPDH was recognized as control) according to Material and Method (9). The results are shown in FIG. 9B (Day 10) and FIG. 9C (Day 13).

As a result of immunofluorescent staining, Oct3/4 positive cells decreased remarkably in the methionine-deprived group. The same result was obtained also in RT-PCT analysis.

Example 8: Influence of Deprivation of Methionine in Feeder Free Differentiation Inducing System An influence of deprivation of methionine in a process of differentiation of human iPS cells into endoderm cells using no feeder cells (mmcM15 cells) on differentiation of human iPS cells into hepatocytes was investigated. Specifically, a 96-well plate coated overnight with Matrigel (BD) diluted 40 times with RPMI1640 culture medium was used for culture. Human iPS cells were treated with Y27632 (10 µM) from 24 hours before seeding, and peeled using 0.25% trypsin. The peeled human iPS cells were seeded on the Matrigel-coated plate at a cell concentration of $1 \times 10^5$ cells/well. The seeded human iPS cells were cultured for 24 hours under 37° C. and 5% $CO_2$ in ES culture medium (ReproStem, ReproCell) containing 10 µM Y27632 and 5 ng/ml bFGF added. After 24 hours, human iPS cells were washed once with PBS, then, the culture medium was changed to an endoderm differentiation culture medium (Day 0). The endoderm differentiation culture medium was changed every other day until Day 8 of culturing, and human iPS cells were cultured under 37° C. and 5% $CO_2$. On Day 8 of culturing, the culture medium was changed to a methionine-deprived culture medium (δMet culture medium) or a control culture medium. Human iPS cells were cultured until Day 10 of culturing using a methionine-deprived culture medium or a control culture medium. On Day 10 of culturing, human iPS cells were subjected to immunofluorescent staining, and positive cells for an endoderm differentiation marker (Sox17) and an undifferentiation marker (Oct3/4) were analyzed. On Day 10 of culturing, the culture medium was changed to a liver differentiation culture medium (2000KSR-DMEM culture medium), and after that, the culture medium was changed every other day.

Figure 10:
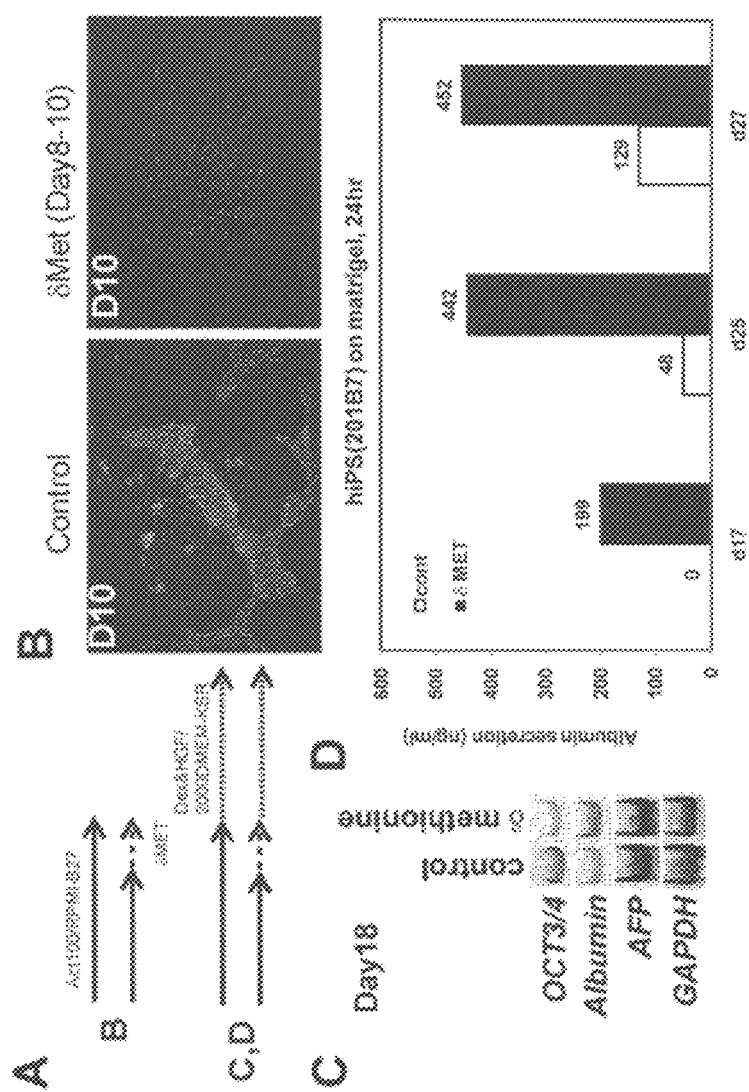
FIG. 10 represents the results of examination of an influence of methionine deprivation in the feeder free differentiation induction system.

Cells on Day 10 of culturing were subjected to immunofluorescent staining with an anti-Sox17 antibody and an anti-Oct3/4 antibody. The results are shown in FIG. 10B. It was confirmed that deprivation of methionine during Day 8 to Day 10 had an effect of removing undifferentiated cells also in a feeder free culture system, like the differentiation inducing method using M15 cells.

Cells on Day 18 of culturing were subjected to RT-PCR for expressions of Oct3/4, albumin and AFP (expression of GAPDH was used as control). The results are shown in FIG. 10C. It was confirmed that expression of an undifferentiated cell marker Oct3/4 decreased remarkably, while expression of albumin as a liver marker increased, in the methionine-deprived group. The albumin secretion amount was measured on Day 17, Day 25 and Day 27. The albumin amount in a culture solution 24 hours after change of the culture medium was measured on Day 17, Day 25 and Day 27, and the amount of albumin secreted in one day was quantified. The results are shown in FIG. 10D. In human iPS cells cultured in the methionine-deprived culture medium (black bar), remarkably higher albumin secretion activity was shown as compared with control (white bar).

Example 9: Influence of Proline Addition on Differentiation of Human iPS Cells into Hepatocytes Example 9-1

For investigating an influence of a proline-added differentiation culture medium on differentiation into hepatocytes, differentiation of human iPS cells into liver precursor cells was induced using a liver differentiation culture medium containing proline added at a concentration of 1 mM.

On a gelatin-coated 96-well plate, mmcM15 cells were seeded as supporting cells. Human iPS cells were treated with Y27632 (10 µM) from 24 hours before seeding, and peeled using 0.25% trypsin. The peeled human iPS cells were seeded on mmcM15 cells at a cell concentration of $1 \times 10^4$ cells/well. The seeded human iPS cells were cultured for 24 hours under 37° C. and 5% $CO_2$ in ES culture medium containing Y27632 and bFGF added. After 24 hours, the culture medium was changed to an endoderm differentiation culture medium (Day 0).

In the same manner as in Example 3, the endoderm differentiation culture medium was changed every other day and human iPS cells were cultured under 37° C. and 5% $CO_2$, from the day of initiation of culturing (Day 0) to Day 8. On Day 8, the culture medium was changed to a methionine-deprived culture medium or a control culture medium. Human iPS cells were cultured until Day 10 using a methionine-deprived culture medium or a control culture medium.

Figure 11:
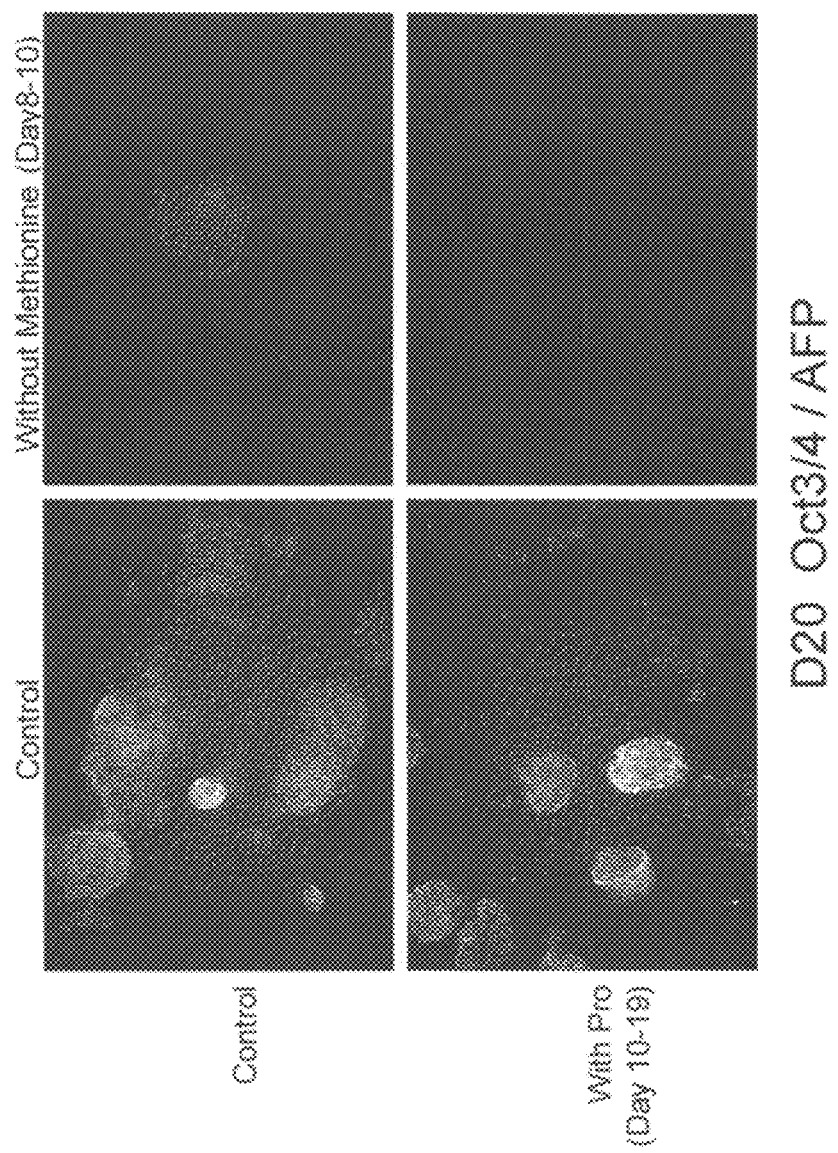
FIG. 11 represents the results of examination of an influence of proline addition on differentiation of human iPS cells into liver cells. It represents the results of immunofluorescent staining with an anti-Oct3/4 antibody and an anti-AFP antibody, of cells cultured for 20 days using each differentiation culture medium. The upper stage represents the control group and the lower stage represents the proline-added group. The left column represents the control group and the right column represents the methionine-deprived group. Green represents AFP positive cells and red represents Oct3/4 positive cells.

On Day 10, the culture medium was changed to a liver differentiation culture medium (2000KSR-DMEM culture medium, control culture medium) or Pro-containing 2000KSR-DMEM culture medium obtained by further adding 1 mM proline to a control culture medium, and human iPS cells were cultured until Day 19 under 37° C. and 5% $CO_2$. During Day 10 to Day 19, the culture medium was changed every other day. On Day 19, human iPS cells were subjected to immunofluorescent staining with an anti-Oct3/4 antibody and an anti-AFP antibody. The results are shown in FIG. 11.

In the methionine-deprived group, AFP positive cells were present uniformly and Oct3/4 positive cells decreased as compared with the control group. In the proline-added group, the number of AFP positive cells was larger and Oct3/4 positive cells decreased as compared with the control group. In the methionine-deprived and proline-added group, an increase of AFP positive cells and a remarkable reduction of Oct3/4 positive cells were recognized.

Example 9-2

An experiment was conducted in the same manner as in Example 9-1 excepting the addition amount of proline was changed from 1 mM to 10 mM. Also when proline was added at a concentration of 10 mM, the same result as in the case of 1 mM addition was obtained.

Figure 12:
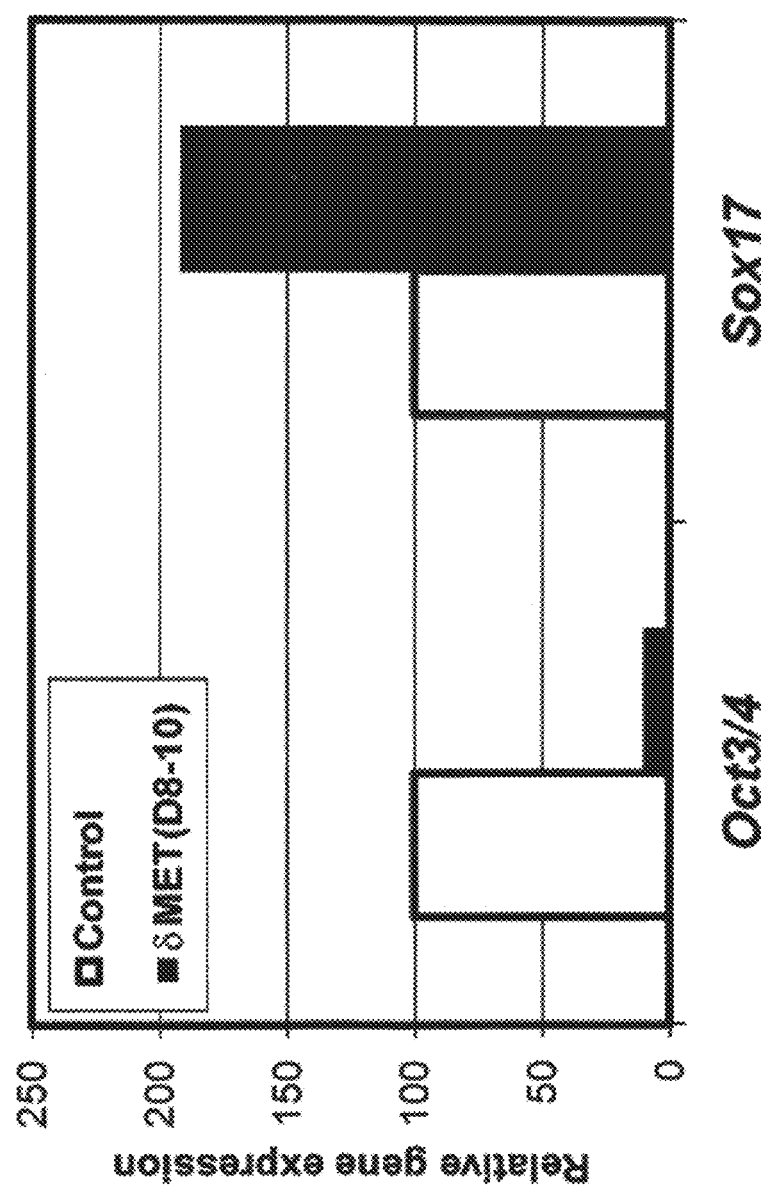
FIG. 12 represents the results of examination of an influence of amino acid deprivation on differentiation into endoderm cells using human ES cells. On Day 8 of culturing, the culture medium was changed to an amino acid-deprived culture medium, and human ES cells were cultured until Day 10, and gene expression of an endoderm differentiation marker (Sox17) and an undifferentiation marker (Oct3/4) were quantitatively analyzed using a real time PCR method, the analyzed results being shown in FIG. 12.

Example 10: Influence of Amino Acid on Differentiation into Endoderm Cells Using Human ES Cells In the same manner as in Reference Example 1, human ES cells (khES3) were differentiated into endoderm cells. Here, during Day 8 to Day 10 of culturing, human ES cells were cultured in a methionine-deprived culture medium, like the case of human iPS cells. On Day 10, gene expressions of an endoderm undifferentiation marker (Sox17) and an undifferentiation marker (Oct3/4) were quantitatively analyzed using a real time PCR method. The results are shown in FIG. 12. By culturing in a methionine-deprived culture medium on Day 8 to Day 10 of culturing, expression of an undifferentiation marker Oct3/4 decreased remarkably, and expression of an endoderm marker Sox17 increased remarkably.

From these results, it was shown that the effect of an amino acid-deprived culture medium is effective also for human ES cells.

Figure 13:
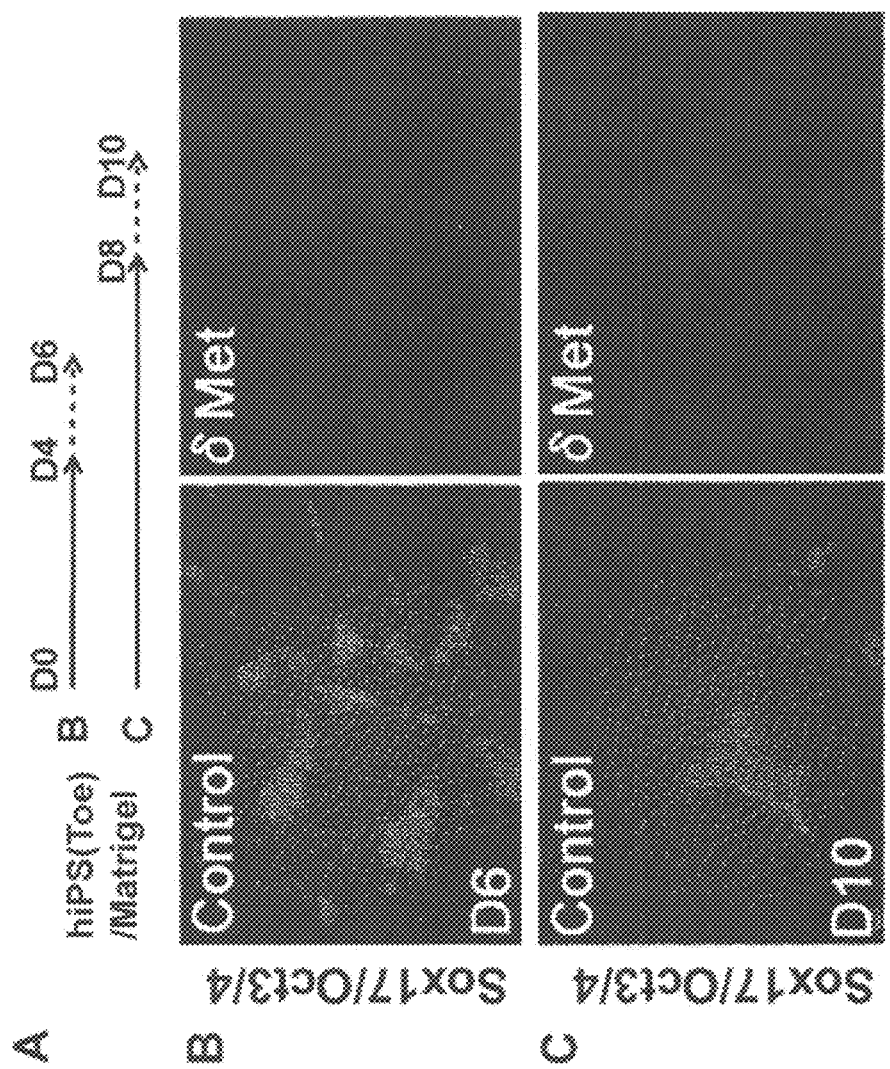
FIG. 13 represents the results of examination of an influence of culturing in a methionine-deprived culture medium on Days 4 to 6 and Days 8 to 10 on differentiation into endoderm cells using human iPS cells (Toe cell line).

Example 11: Effect of Methionine-Deprived Culture Medium During Day 4 to Day 6 on Differentiation of Human iPS Cells in Feeder Free System In the same manner as in Example 8, iPS cells (Toe cell line) were differentiated into endoderm cells in a system using no feeder cell. Here, culturing in a methionine-deprived culture medium was conducted on Day 8 to Day 10, and Day 4 to Day 6, and cells on Day 10 and Day 6 were subjected to immunofluorescent staining with an anti-Sox17 antibody and an anti-Oct3/4 antibody, respectively. The results are shown in FIG. 13.

As a result, it was confirmed that an effect of removal of undifferentiated cells was obtained also by culture in a methionine-deprived culture medium on Day 4 to Day 6, like culture on Day 8 to Day 10.

Example 12: Influence of Deprivation of Methionine in Process of Maintenance Culture of Human iPS Cells An influence of deprivation of methionine in the process of maintenance culture of human iPS cells on growth of human iPS cells was examined. Specifically, a 96-well plate coated overnight with Matrigel (BD) diluted 40 times with RPMI1640 culture medium was used for culture. Human iPS cells were treated with Y27632 (10 µM) from 24 hours before seeding, and peeled using 0.25% trypsin. The peeled human iPS cells were seeded on the Matrigel-coated plate at a cell concentration of $5 \times 10^4$ cells/well. The seeded human iPS cells were cultured for 24 hours under 37° C. and 5%

$CO_2$ in ES culture medium (CSTI-7, Cell Science & Technology Institute, Inc.) containing 10 μM Y27632 and 5 ng/ml bFGF added. After 24 hours, human iPS cells were washed once with PBS, then, the culture medium was changed to CSTI-7 culture medium (Complete), a culture medium obtained by depriving CSTI-7 of methionine (ΔMet) and a culture medium obtained by adding methionine at various concentrations to ΔMet (ΔMet+Met) (Day 0). Human iPS cells were cultured under 37° C. and 5% $CO_2$ until Day 2 of culturing. On Day 2 of culturing, the number of human iPS cells was quantified using PrestBlue (Invitrogen).

Figure 14:
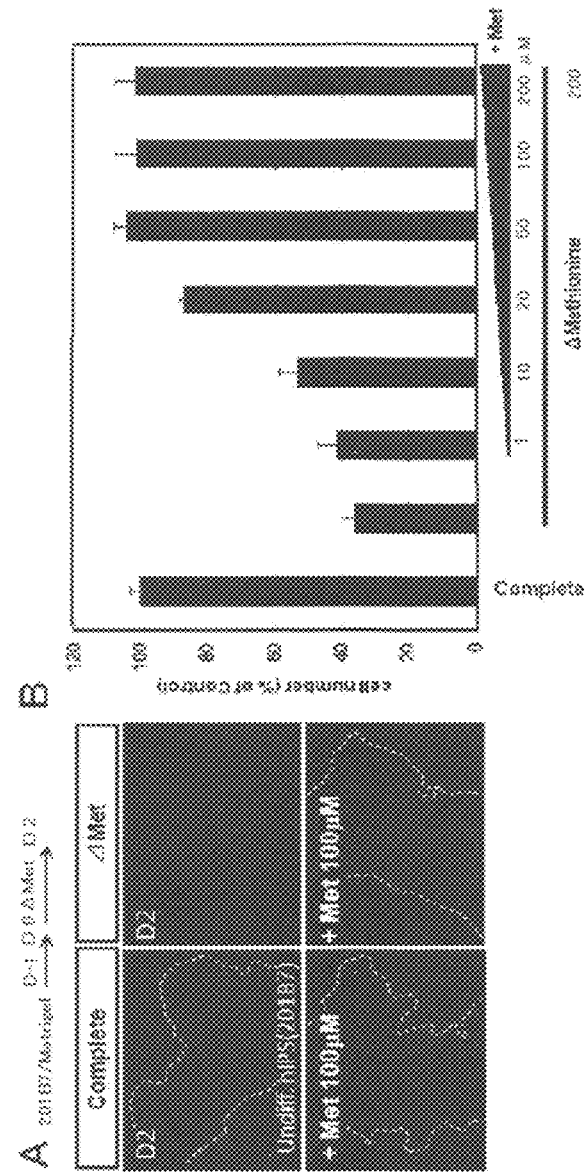
FIG. 14 represents the results of examination of an influence of methionine deprivation on growth of human in cells in the maintenance culture process of human iPS cells.

The results are shown in FIG. 14. FIG. 14A shows bright-field images under various conditions on Day 2 of culturing. By methionine deprivation, colonies of human iPS cells decreased. FIG. 4B represents the results of quantification of the number of cells after methionine deprivation. It was confirmed that growth of (undifferentiated) iPS cells is prevented by methionine deprivation.

Example 13: Influence of Treating Time in Methionine-Deprived Culture Medium For investigating an influence of treating time of a methionine-deprived culture medium in differentiation into endoderm cells, the culture medium was changed to a methionine-deprived culture medium on Day 8 of culturing, and cell proliferation and apoptosis after 5 hours, 24 hours and 48 hours were evaluated. Specifically, mmcM15 cells were seeded as supporting cells on a gelatin-coated 96-well plate. Human iPS cells were treated with Y27632 (10 μM) from 24 hours before seeding, and peeled using 0.25% trypsin. The peeled human iPS cells were seeded on mmcM15 cells at a cell concentration of $1\times10^4$ cells/well. The seeded human iPS cells were cultured for 24 hours under 37° C. and 5% $CO_2$ in ES culture medium containing Y27632 and bFGF added. After 24 hours, the culture medium was changed/to an endoderm differentiation culture medium (Day 0).

Figure 15:
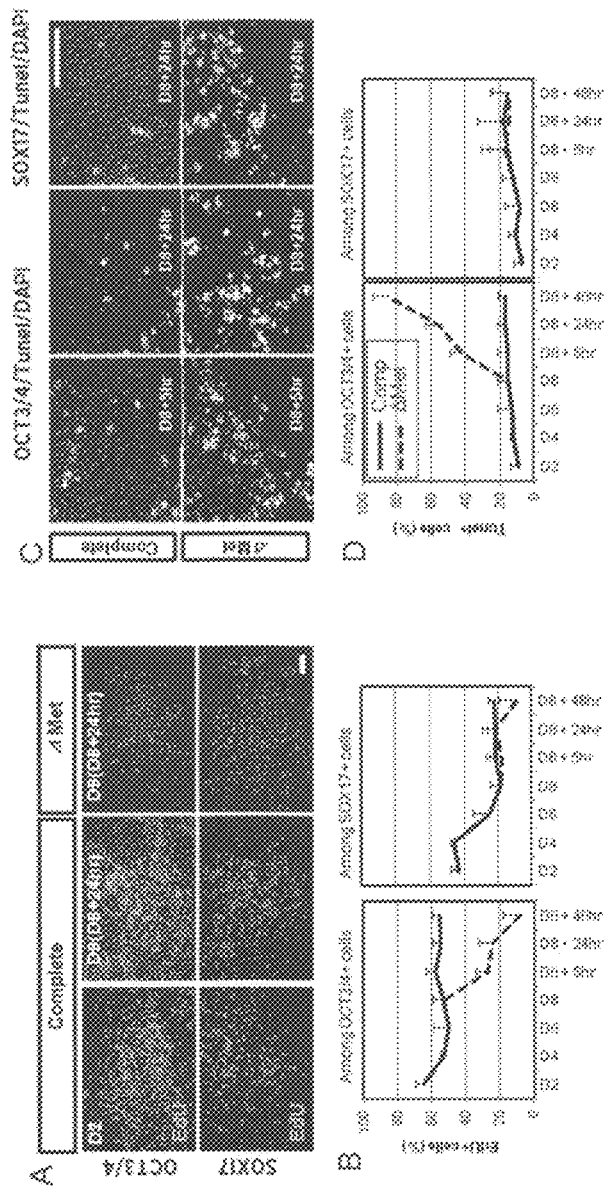
FIG. 15 represents the results of evaluation of cell proliferation and apoptosis after various treatment times in a methionine-deprived culture medium.
Figure 16:
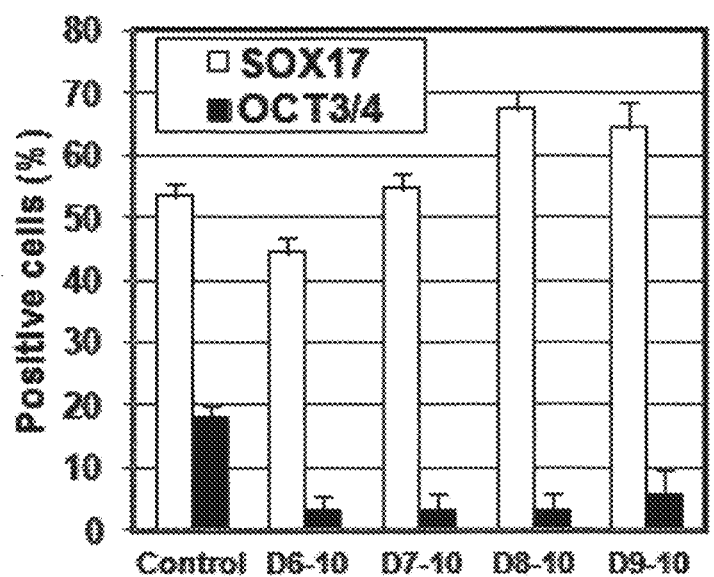
FIG. 16 is a graph representing the proportions of human iPS cells cultured at various methionine deprivation periods (X axis), immunofluorescent-stained with an anti-Sox17 antibody and an anti-Oct3/4 antibody.

The endoderm differentiation culture medium was changed every other day and human iPS cells were cultured under 37° C. and 5% $CO_2$ from the day of initiation of culture (Day 0) to Day 8. On Day 8, the culture medium was changed to a methionine-deprived culture medium or a control culture medium. Human iPS cells were cultured until Day 10 using a methionine-deprived culture medium or a control culture medium. Cell proliferation 5 hours, 24 hours and 48 hours after change of the culture medium on Day 8 was evaluated using Click-iT EdU cell proliferation assay kit (Invitrogen), and apoptosis was evaluated using In Situ Cell Death Detection Kit (Roche). Further, to study the period of methionine deprivation, the deprivation period was altered to D6-10, D7-10, D8-10 and D9-10 and, Oct3/4 and Sox17 positive cells on Day 10 of culturing were counted. The results are shown in FIG. 15 and FIG. 16.

FIG. 15A shows the results of evaluation by antibody staining of EdU uptake in Oct3/4 and Sox17 positive cells, and the quantification results are shown in graphs of FIG. 15B. Five hours after methionine deprivation, cell proliferation was inhibited significantly, and the effect was remarkable for Oct3/4 positive cells. FIG. 15C shows the results of evaluation by Tunel staining of apoptosis in Oct3/4 and Sox17 positive cells, and the quantification results are shown in graphs of FIG. 15D. Five hours after methionine deprivation, apoptosis was induced specifically in Oct3/4 positive cells.

To study the period of methionine deprivation, the deprivation period was altered to D6-10, D7-10, D8-10 and D9-10, and Oct3/4 and Sox17 positive cells on Day 10 of culturing were counted. The results are shown in FIG. 16. In deprivation from Day 6 of culturing, a decrease in Sox17 positive cells was confirmed.

Example 14: Influence of Methyl Donor-Deprived Culture Medium

For investigating an influence of a methionine and methyl donor-deprived culture medium on differentiation into endoderm cells, a culture medium was deprived of methionine and methyl donors on Day 8 of differentiation, and cells were cultured until Day 10 and the numbers of Oct3/4 and Sox17 positive cells were evaluated by antibody staining. Specifically, mmcM15 cells were seeded as supporting cells on a gelatin-coated 96-well plate. Human iPS cells were treated with Y27632 (10 μM) from 24 hours before seeding, and peeled using 0.25% trypsin. The peeled human iPS cells were seeded on mmcM15 cells at a cell concentration of $1\times10^4$ cells/well. The seeded human iPS cells were cultured for 24 hours under 37° C. and 5% $CO_2$ in ES culture medium containing Y27632 and bFGF added. After 24 hours, the culture medium was changed to an endoderm differentiation culture medium (Day 0). The endoderm differentiation culture medium was changed every other day and human iPS cells cultured under 37° C. and 5% $CO_2$ from the day of initiation of culture (Day 0) to Day 8. On Day 8, the culture medium was changed to various culture media. One obtained by removing ethionine•folate•vitamin B12•betaine•choline from the culture medium was used as a methyl donor-deprived culture medium. Human iPS cells were cultured until Day 10 using various culture media, and Oct3/4 and Sox17 positive cells were counted.

Figure 17:
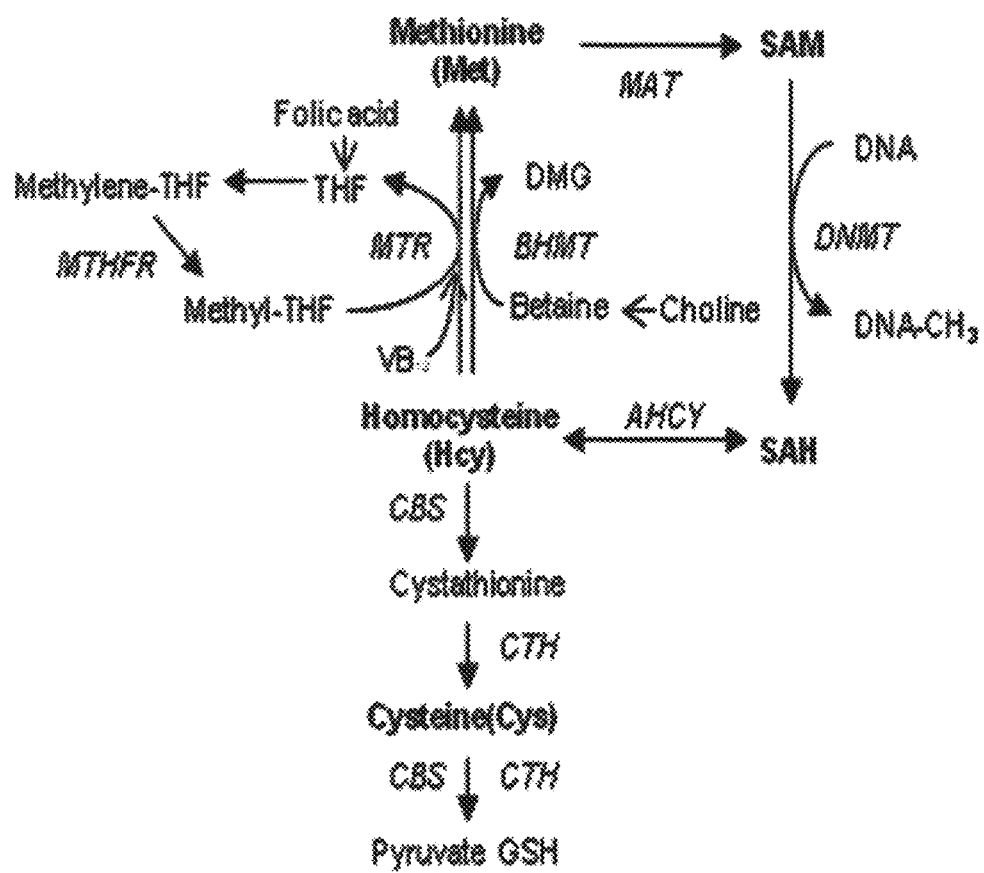
FIG. 17 represents a metabolic pathway of methionine in a living organism.
Figure 18:
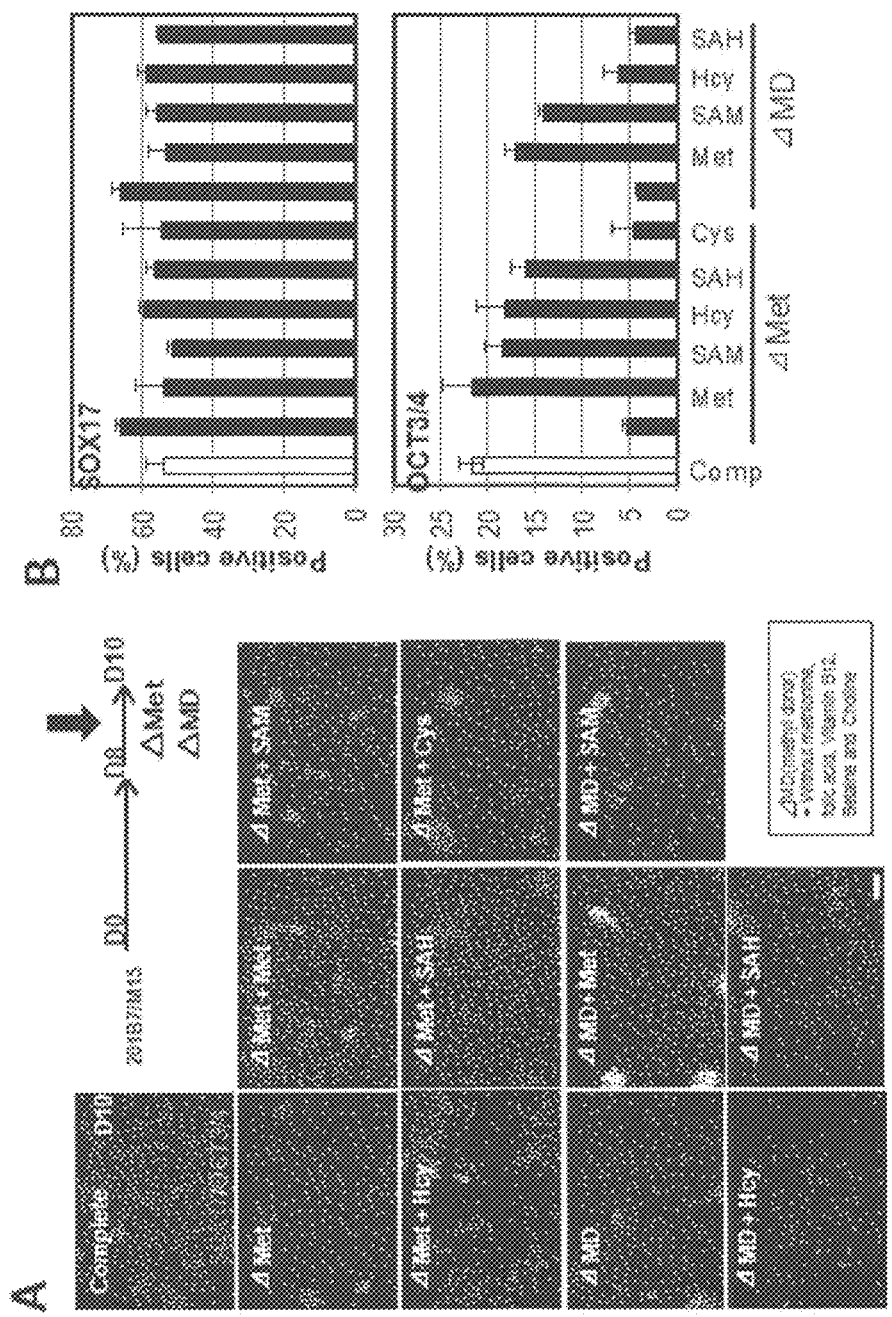
FIG. 18 represents the results of examination of an influence of a methionine and/or methyl donor-deprived culture medium on differentiation of human iPS cells into endoderm cells.

As shown in FIG. 17, methionine is bio-synthesized from S-adenosylmethionine (SAM), S-adenosylhomocystein (SAH), homocysteine (Hcy) using vitamin B12 (VB12), folic acid, choline, betaine in a living body. It is known that methionine is metabolized to give cysteine (Cys). Then, Met, SAM, Hcy, SAH and Cys were added to a methionine-deprived culture-medium (ΔMet) or a methyl donor-deprived culture medium (ΔMD) to test if this addition could inhibit the action of reducing Oct3/4 positive cells owing to methionine deprivation. The results are shown in FIG. 18. In the figure, δMD denotes a culture medium not containing methionine, folic acid, vitamin B12, betaine and choline as a methyl donor. FIG. 18A represents stained images of Oct3/4 and Sox17 positive cells, and the quantification results are shown in graphs of FIG. 18B. As shown in FIG. 18B, by adding Met, SAM, Hcy and SAH, the effect of reducing Oct3/4 positive cells is inhibited, while addition of Cys has no influence.

Further, the same investigation was carried out in a system in which methionine synthesis is not performed using a methyl donor-deprived culture medium, to find that addition of Met and SAM inhibited the effect of reducing Oct3/4 positive cells, while addition of Hcy and SAH had not influence. From this result, it was suggested that a reduction of undifferentiated cells owing to methionine deprivation is ascribable to disappearance of SAM in cells.

The above-described detailed descriptions simply explain the object and the subject matter of the present invention, and do not limit the scope of the appended claims. Without deviating from the scope of the appended claims, various alterations and substitutions for embodiments described are apparent for those skilled in the art based on teachings described in the present specification.

INDUSTRIAL APPLICABILITY

According to the present invention, differentiation of pluripotent stem cells such as ES cells and iPS cells can be induced efficiently. ES cells or iPS cells differentiated by the present invention contain no or trace amount of mixed undifferentiated cells, thus, a risk due to mixing of undifferentiated cells can be avoided.

Therefore, cells differentiated by the present invention are useful for analysis of various tissue cells and for regenerative medicine.

The invention claimed is:

1. A method of inducing differentiation of pluripotent stem cells into cells expressing endoderm, mesoderm or ectoderm markers, comprising the following steps:
   (a) obtaining human pluripotent stem cells, wherein the human pluripotent stem cells are human embryonic stem cell (hESCs) or human induced pluripotent stem cells (hiPSCs),
   (b) culturing the human pluripotent stem cells of step (a) in a culture medium comprising threonine, methionine, valine, leucine, isoleucine, phenylalanine, tryptophan, lysine, histidine, cysteine, tyrosine and arginine, to produce cells expressing endoderm, mesoderm or ectoderm markers, and
   (c) culturing the cells of step (b) in a methionine-deprived culture medium comprising threonine, valine, isoleucine, phenylalanine, tryptophan, lysine and histidine for at least 5 hours and not more than 4 days, to eliminate Oct3/4 undifferentiated pluripotent stem cells, thereby producing an enriched population of induced differentiated cells expressing endoderm, mesoderm or ectoderm markers.

2. The method of claim 1, wherein the cells of step (c) are further cultured in an endoderm differentiation culture medium comprising Activin A and B27 to produce endoderm cells expressing Sox17.

3. The method according to claim 2, wherein the differentiated endoderm cells are further cultured in hepatocyte differentiation culture medium, comprising dexamethasone, human recombinant hepatocyte growth factor (HGF), nicotinamide and ascorbic acid, to produce hepatocytes expressing alpha-fetoprotein (AFP).

4. The method according to claim 2, wherein the differentiated endoderm cells are further cultured in a pancreas differentiation culture medium, comprising glucose, retinoic acid, FGF10, KAAF-cyclomine and B27, to produce pancreatic cells expressing PDX1.

5. The method according to claim 3, wherein the hepatocyte differentiation culture medium contains proline added in an amount of 1 mM or more and 10 mM or less.

6. The method according to claim 4, wherein the pancreas differentiation culture medium contains proline added in an amount of 1 mM or more and 10 mM or less.

* * * * *